(12) United States Patent
Feng et al.

(10) Patent No.: US 10,624,599 B2
(45) Date of Patent: Apr. 21, 2020

(54) SYSTEMS AND METHODS FOR MOTION SIGNAL CORRECTION

(71) Applicant: SHANGHAI UNITED IMAGING HEALTHCARE CO., LTD., Shanghai (CN)

(72) Inventors: Tao Feng, Houston, TX (US); Wentao Zhu, Houston, TX (US); Jizhe Wang, Houston, TX (US); Youjun Sun, Shanghai (CN); Hongdi Li, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 439 days.

(21) Appl. No.: 15/664,011

(22) Filed: Jul. 31, 2017

(65) Prior Publication Data

US 2019/0029626 A1   Jan. 31, 2019

(51) Int. Cl.
| | |
|---|---|
| *G01T 1/166* | (2006.01) |
| *G06K 9/00* | (2006.01) |
| *A61B 6/00* | (2006.01) |
| *G06T 7/68* | (2017.01) |
| *G06T 7/246* | (2017.01) |
| *G06T 7/33* | (2017.01) |
| *A61B 6/03* | (2006.01) |
| *G06T 11/00* | (2006.01) |

(52) U.S. Cl.
CPC ............ *A61B 6/5217* (2013.01); *A61B 6/037* (2013.01); *G06T 7/246* (2017.01); *G06T 7/33* (2017.01); *G06T 7/68* (2017.01); *G06T 11/005* (2013.01); *A61B 6/541* (2013.01); *G06T 2207/10072* (2013.01); *G06T 2207/10104* (2013.01); *G06T 2207/10108* (2013.01); *G06T 2211/412* (2013.01)

(58) Field of Classification Search
USPC ....... 382/100, 103, 107, 128–133, 154, 162, 382/168, 173, 181, 219, 224, 232, 254, 382/274, 276, 286–291; 600/427; 1/1; 250/363.03, 363.04; 378/4, 21
See application file for complete search history.

(56) References Cited

U.S. PATENT DOCUMENTS

| | | | | |
|---|---|---|---|---|
| 6,147,353 A | * | 11/2000 | Gagnon ............... | G01T 1/1648 250/363.04 |
| 6,490,476 B1 | * | 12/2002 | Townsend ............ | A61B 6/032 250/363.03 |

(Continued)

OTHER PUBLICATIONS

Paul J. Schleyer et al., Extension of a Data-driven Gating Technique to 3D, Whole Body PET Studies, Physics in Medicine and Biology, 56:3953-3965, 2011.

(Continued)

*Primary Examiner* — Seyed H Azarian
(74) *Attorney, Agent, or Firm* — Metis IP LLC

(57) ABSTRACT

The present disclosure describes systems and methods for determining whether a motion signal derived from image data relating to a subject is synchronous with the actual motion state of the subject. The method may include determining one or more values of a symmetry related parameter of a motion signal. The method may further include correcting the motion signal if the motion signal is determined flipped.

18 Claims, 16 Drawing Sheets

(56) References Cited

U.S. PATENT DOCUMENTS

| | | | |
|---|---|---|---|
| 8,569,706 B2* | 10/2013 | Thiruvenkadam | A61B 6/037 250/363.03 |
| 9,451,926 B2* | 9/2016 | Kinahan | A61B 6/527 |
| 2012/0078089 A1* | 3/2012 | Wollenweber | A61B 6/5235 600/427 |

OTHER PUBLICATIONS

Ottavia Bertolli et al., Sign Determination Methods for the Respiratory Signal in Data-driven PET Gating, Physics in Medicine and Biology, 62:3204-3220, 2017.
Chi Liu et al., Quiescent Period Respiratory Gating for PET/CT, Medical Physics 37(9):5037-5043, 2010.

* cited by examiner

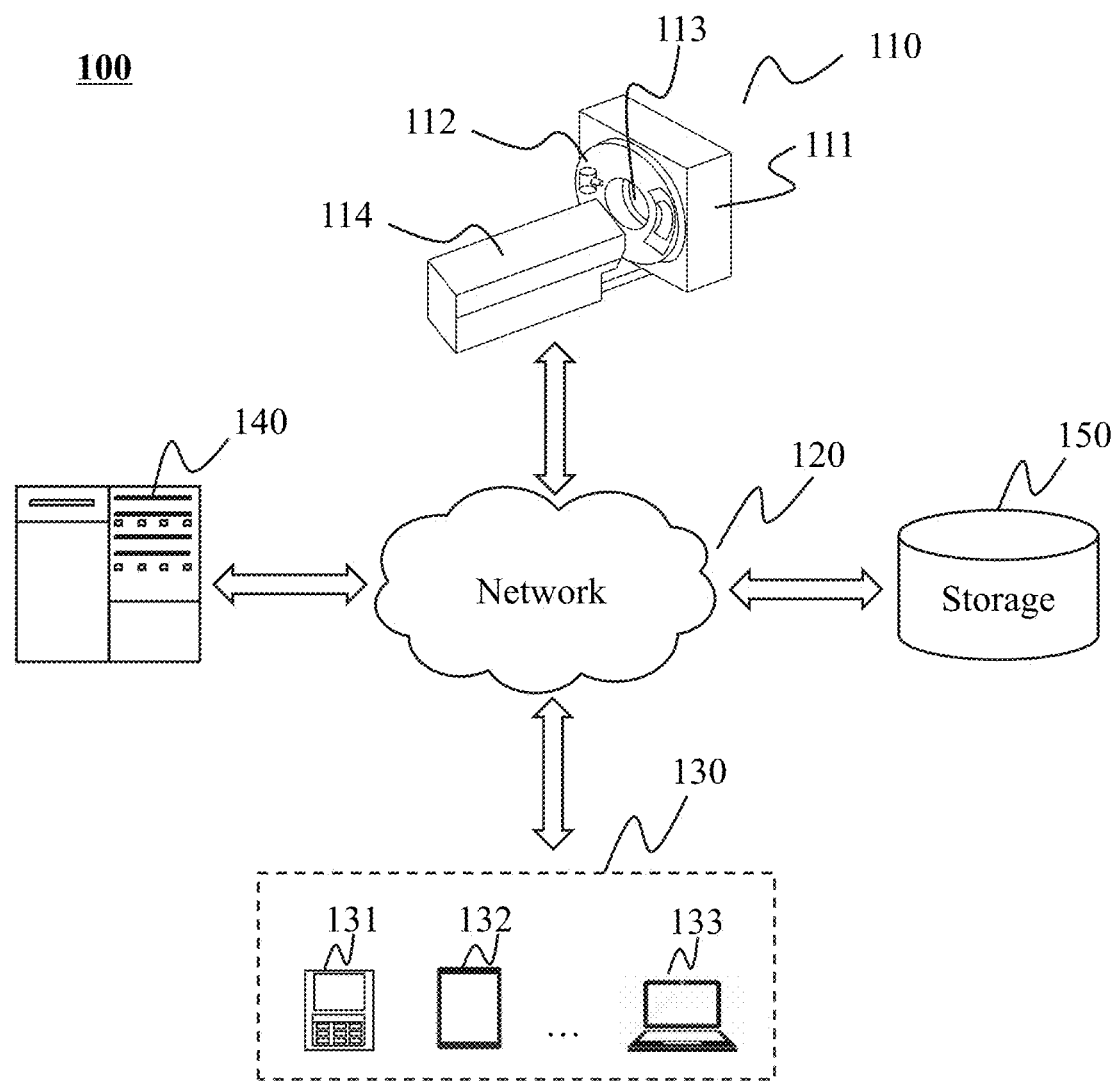
FIG. 1-A

140
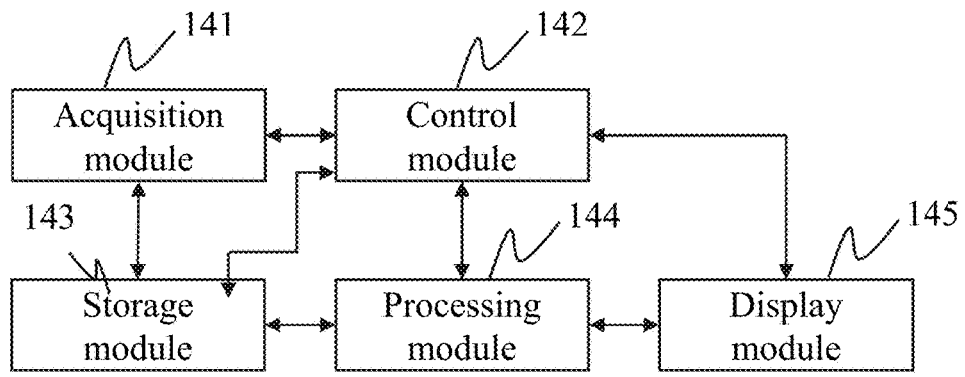
FIG. 1-B
160
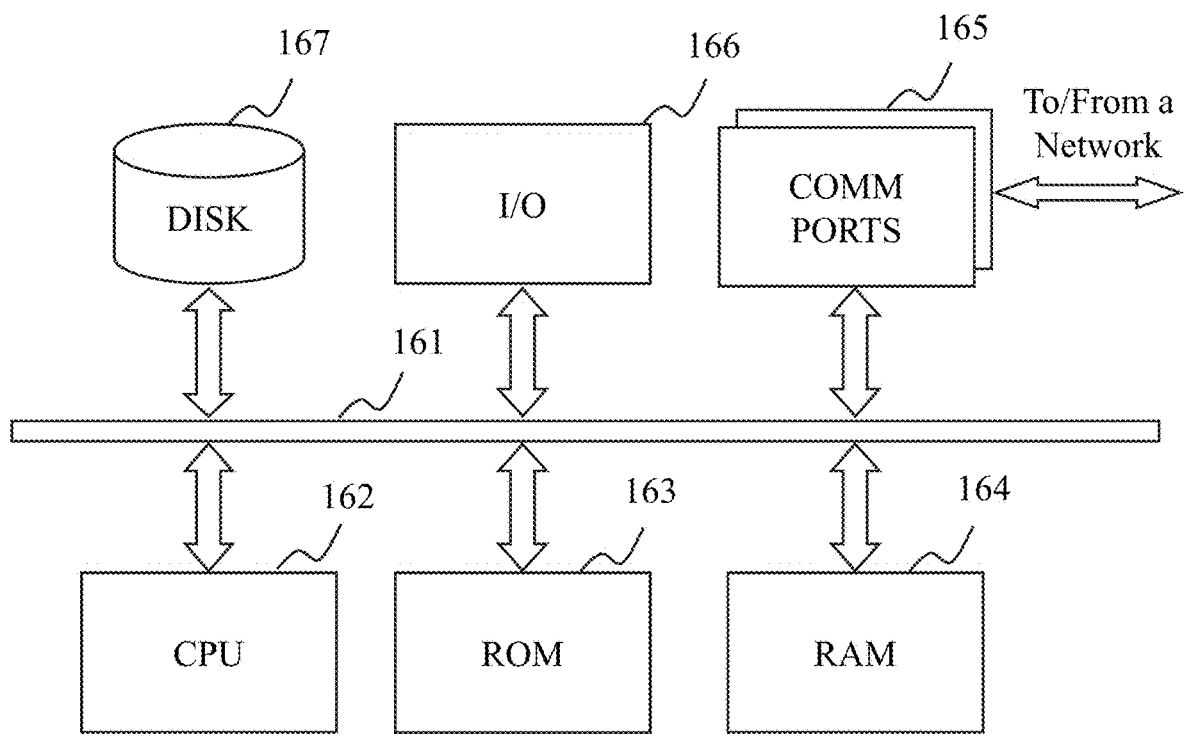
FIG. 1-C

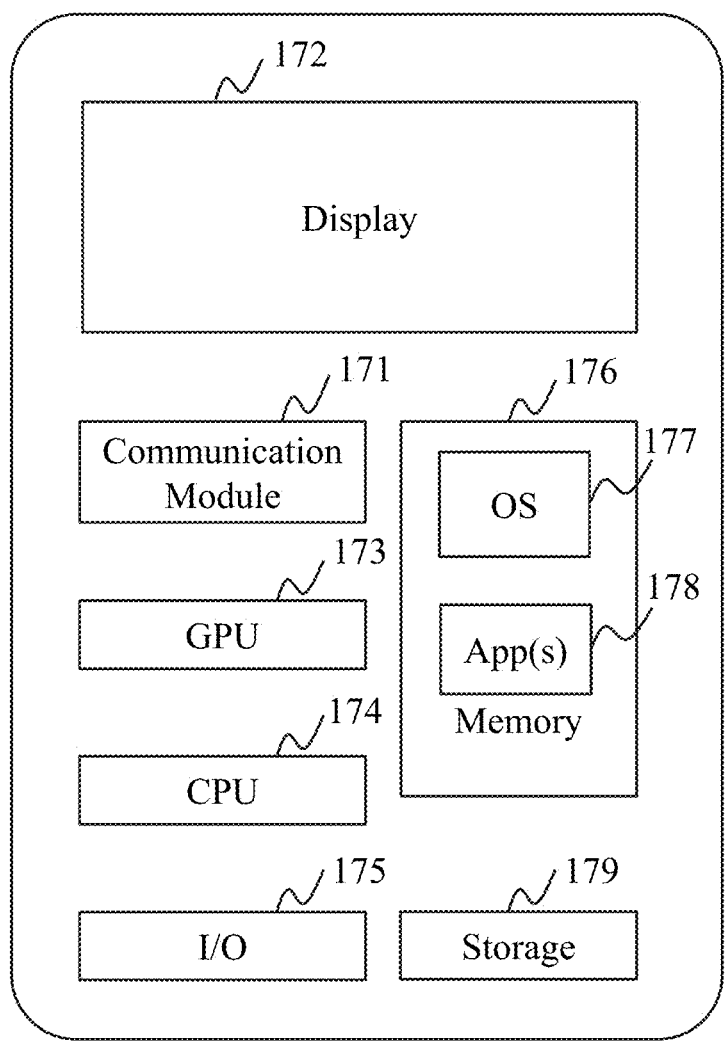
FIG. 1-D

SYSTEMS AND METHODS FOR MOTION SIGNAL CORRECTION

TECHNICAL FIELD

The application generally relates to systems and methods for signal processing, and more specifically relates to systems and methods for correcting a motion signal.

BACKGROUND

Respiratory gating may reduce the effects of respiratory motion in image reconstruction, such as Emission Computed Tomography (ECT) image reconstruction. A respiratory motion signal may be needed for the respiratory gating. In some embodiments, a data-driven technique may be used to extract a respiratory motion signal. Limited by factors including, for example, the algorithm itself applied in a data-driven technique, the field of view of the image scanner used to acquire image data to be analyzed, the data-driven technique may extract respiratory motion signals that have flipped phases. The direct use of such respiratory motion signals may be troublesome for the determination of inspiration/expiration phases of the respiratory motion. Furthermore, the uncertainty on the inspiration/expiration phases of the respiratory motion may cause inaccurate motion correction of an image.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

According to an aspect of the present disclosure, a method for correcting a motion signal is provided. The method may be implemented on at least one machine each of which has at least one processor and storage. The method may include acquiring a motion signal. The method may further include determining one or more values of a symmetry related parameter of the motion signal. The method may further include determining that the motion signal is flipped based on the one or more values of the symmetry related parameter. The method may further include correcting, in response to the determination that the motion signal is flipped, the motion signal.

In some embodiments, the acquiring a motion signal may include acquiring a respiratory motion signal based on Emission Computed Tomography (ECT) data.

In some embodiments, the determining one or more values of a symmetry related parameter of the motion signal may include determining a reference line with respect to the motion signal.

In some embodiments, the motion signal may include a respiratory motion signal, the determining one or more values of a symmetry related parameter of the motion signal may include identifying an end of a candidate inspiration phase (candidate EIP) and an end of a candidate expiration phase (candidate EEP) in the respiratory motion signal based on the reference line, wherein an amplitude of the candidate EIP is a peak amplitude of the respiratory motion signal, and an amplitude of the candidate EEP is a valley amplitude of the respiratory motion signal, wherein the reference line is midway between the candidate EIP and the candidate EEP such that the amplitude of the candidate EIP is equal to the amplitude of the candidate EEP; and determining the one or more values of the symmetry related parameter of the motion signal based on a duration related to the candidate EIP and a duration related to the candidate EEP.

In some embodiments, the motion signal may include a respiratory motion signal, the determining one or more values of a symmetry related parameter of the motion signal may include determining a duration related to a candidate inspiration phase and a duration of a candidate expiration phase based on the reference line, wherein the reference line is such that the duration of the candidate inspiration phase is equal to the duration of the candidate expiration phase; identifying one or more ends related to the candidate inspiration phases (candidate EIPs) and one or more ends of the candidate expiration phase (candidate EEPs); determining a peak amplitude of the one or more candidate EIPs of the motion signal with respect to the reference line, and a valley amplitude of the one or more candidate EEPs of the motion signal with respect to the reference line; and determining the one or more values of the symmetry related parameter of the motion signal based on the peak amplitude and the valley amplitude.

In some embodiments, the motion signal comprising a respiratory motion signal, the determining a reference line of the motion signal may include determining a reference line of the respiratory motion signal based on a first criterion including a combination of an amplitude and a duration of the respiratory motion signal.

In some embodiments, the determining one or more values of a symmetry related parameter of the motion signal may include determining one or more values of the symmetry related parameter of the respiratory motion signal based on a second criterion including a combination of a weighted amplitude and the duration of the respiratory motion signal with respect to the reference line.

In some embodiments, the determining that the motion signal is flipped may include determining credibility of the one or more values of the symmetry related parameter.

In some embodiments, the determining credibility of the one or more values of the symmetry related parameter may include determining whether the one or more values of the symmetry related parameter are below a first threshold; or determining whether a duration of the respiratory motion signal is less than a second threshold; or determining a variation among the one or more values of the symmetry related parameter; or determining whether a signal to noise ratio corresponding to the respiratory motion signal exceeds a third threshold.

In some embodiments, the determining that the motion signal is flipped may include determining, in response to a determination that the one or more values of the symmetry related parameter are incredible, that the respiratory motion signal is flipped based on a plurality of images reconstructed based on the ECT data.

In some embodiments, each frame of the plurality of frames of the ECT data may correspond to a same number of ECT events.

In some embodiments, the determining that the respiratory motion signal is flipped based on a plurality of images reconstructed based on the ECT data may include gating, based on the respiratory motion signal, the ECT data into a plurality of frames; reconstructing the plurality of images, an image of the plurality of images corresponding to a frame of the plurality of frames of the ECT data; registering at least two of the plurality of images; determining a motion of a point of interest based on the registration; and determining that the respiratory motion signal is flipped based on the motion of the point of interest.

In some embodiments, each frame of the plurality of frames of the ECT data may correspond to a same amplitude interval, or a same time interval.

In some embodiments, the registering at least two of the plurality of images may include registering the at least two of the plurality of images based on an approach of sum square error (SSE).

According to an aspect of the present disclosure, a method for correcting a motion signal is provided. The system may include an acquisition module that is configured to obtain ECT data relating to a subject. The system may further include a processing module. The processing module may include a respiratory motion signal acquisition unit that is configured to acquire a respiratory motion signal based on the ECT data. The processing module may further include a symmetry determination unit that is configured to determine one or more values of a symmetry related parameter of the respiratory motion signal. The processing module may further include a flip determination unit that is configured to determine that the respiratory motion signal is flipped based on the one or more values of the symmetry related parameter. The processing module may further include a correction unit that is configured to correct, in response to the determination that the respiratory motion signal is flipped, the respiratory motion signal.

According to an aspect of the present disclosure, a method for correcting a motion signal is provided. The method may be implemented on at least one machine, each of which has at least one processor and storage. The method may include acquiring ECT data of a subject, and determining a motion signal based on the ECT data. The method may further include determining that the motion signal is flipped. The method may further include correcting the motion signal if the determination that the motion signal is flipped.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A is a schematic diagram illustrating an exemplary imaging system according to some embodiments of the present disclosure;

FIG. 1-B is a block diagram illustrating an exemplary processing engine according to some embodiments of the present disclosure;

FIG. 1-C is a schematic diagram illustrating an exemplary computing device according to some embodiments of the present disclosure;

FIG. 1-D is a schematic diagram illustrating exemplary hardware and/or software components of an exemplary mobile device according to some embodiments of the present disclosure;

DETAILED DESCRIPTION

Figure 2:
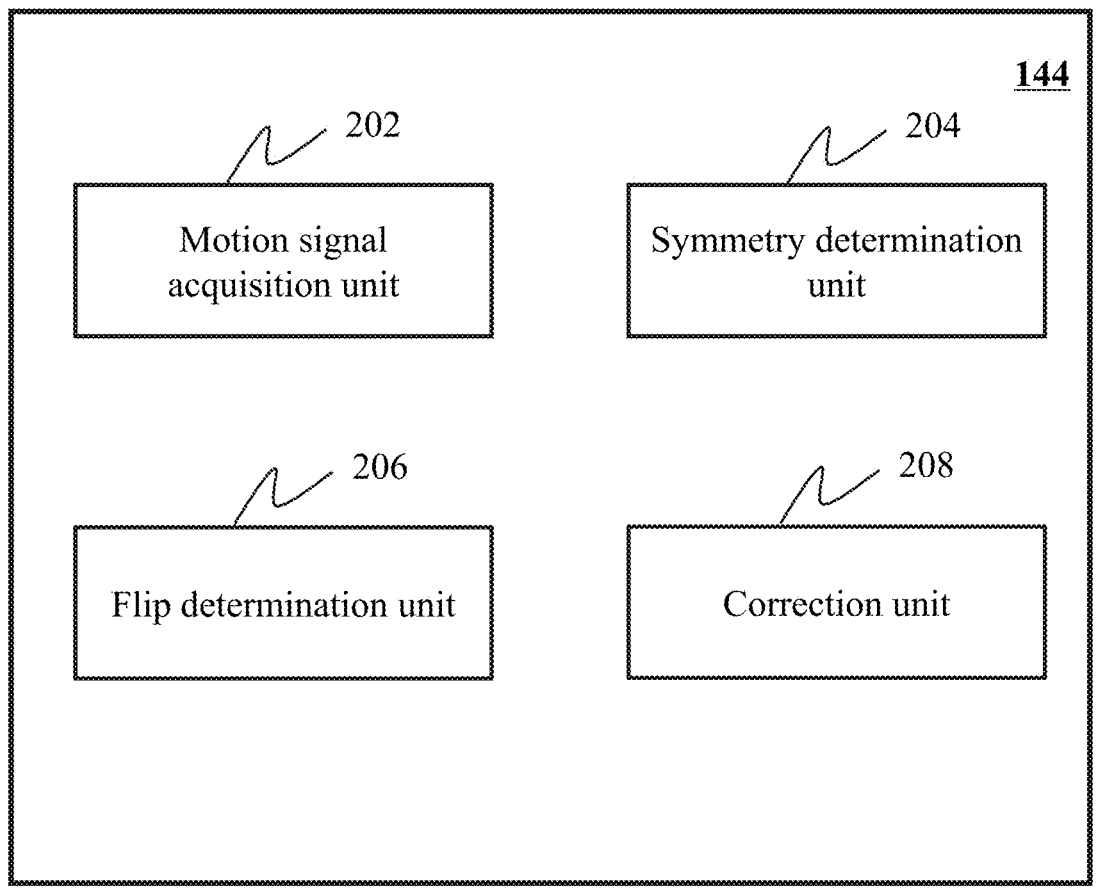
FIG. 2 is a block diagram illustrating an exemplary processing module according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure describes systems and methods for determining whether a motion signal derived from image data relating to a subject is synchronous with the actual motion state of the subject. For example, a determination may be made as to whether the motion signal derived from the image data is flipped based on one or more values of a symmetry related parameter of the motion signal. Furthermore, in response to the determination that the motion signal is flipped, the motion signal may be corrected.

FIG. 1-A is a schematic diagram illustrating an exemplary imaging system 100 according to some embodiments of the present disclosure. The imaging system 100 may include an emission computed tomography (ECT) system, such as, for example, a positron emission tomography (PET) system, a single photon emission computed tomography (SPECT) system, a multi-modality system, etc. The imaging system 100 may include a multi-modality system including, for example, a computed tomography-positron emission tomography (CT-PET) system, a magnetic resonance-positron emission tomography (MR-PET) system, etc. In some embodiments, the multi-modality system may include modules and/or components for performing ECT imaging and/or related analysis. Merely by way of example, the imaging system 100 may include an ECT scanner 110, a network 120, one or more terminals 130, a processing engine 140, and a storage 150.

In some embodiments, the ECT scanner 110, the processing engine 140, the storage 150, and/or the terminal(s) 130 may be connected to and/or communicate with each other via a wireless connection (e.g., the network 120), a wired connection, or a combination thereof. The connection between the components in the imaging system 100 may be variable. Merely by way of example, the ECT scanner 110 may be connected to the processing engine 140 through the network 120, as illustrated in FIG. 1. As another example, the ECT scanner 110 may be connected to the processing engine 140 directly. As a further example, the storage 150 may be connected to the processing engine 140 through the network 120, as illustrated in FIG. 1, or connected to the processing engine 140 directly. As still a further example, a terminal 130 may be connected to the processing engine 140 through the network 120, as illustrated in FIG. 1, or connected to the processing engine 140 directly.

The ECT scanner 110 may include a gantry 111, a detector 112 mounted on the gantry 111, a detection region 113, and a subject table 114.

The detector 112 may detect radiation events (e.g., gamma photons) emitted from the detection region 113. At least a portion of the radiation events may originate from a subject placed in the detection region 113. In some embodiments, the detector 112 may include a plurality of detector units. The detector units may be implemented in any suitable manner, for example, in a ring, in a rectangle, or in an array. In some embodiments, the detector units may include one or more crystal elements and/or one or more photomultiplier tubes (PMT). A PMT as employed in the present disclosure may be a single-channel PMT or a multi-channel PMT. The subject table 114 may transfer a patient into the detection region 113.

In some embodiments, the detected radiation events may be stored or archived in a storage (e.g., the storage 150 or a storage module in the processing engine 140), processed by the processing engine 140, or transferred to an external processing and/or storage device (e.g., a cloud server) via a cable, or a wired or wireless network.

The network 120 may include any suitable network that can facilitate exchange of information and/or data within the imaging system 100 or between a component of the imaging system 100 and an external device. In some embodiments, one or more components of the imaging system 100 (e.g., the ECT scanner 110, the terminal 130, the processing engine 140, the storage 150, etc.) may exchange information and/or data with one or more other components of the imaging system 100 via the network 120. For example, the processing engine 140 may receive image data from the ECT scanner 110 directly or via the network 120. As another example, the processing engine 140 may obtain user instructions from the terminal 130 via the network 120.

The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the ECT system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Exemplary smart home device may include a smart lighting device, a control device of an intelligent electrical apparatus, a smart monitoring device, a smart television, a smart video camera, an interphone, or the like, or any combination thereof. Exemplary wearable device may include a bracelet, a footgear, eyeglasses, a helmet, a watch, clothing, a backpack, a smart accessory, or the like, or any combination thereof. Exemplary mobile device may include a mobile phone, a personal digital assistance (PDA), a gaming device, a navigation device, a point of sale (POS) device, a laptop, a tablet computer, a desktop, or the like, or any combination thereof. Exemplary virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be implemented on the processing engine 140.

The processing engine 140 may process image data (e.g., raw scanning data, a plurality of image slices) obtained from the ECT scanner 110, the terminal 130, and/or the storage 150. In some embodiments, the processing engine 140 may be a single server or a server group. The server group may be centralized or distributed. In some embodiments, the processing engine 140 may be local to or remote from other components in the imaging system 100. The processing engine 140 may access ECT data produced by the ECT scanner 110, stored by the terminal 130, the storage 150, an external storage device via, for example, the network 120. Alternatively, the processing engine 140 may be directly connected to the ECT scanner 110, the terminal 130, and/or the storage 150 to access the image data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device having one or more components as illustrated in FIG. 1-C.

The storage 150 may store data, instructions, and/or any other information. In some embodiments, the storage 150 may store data obtained from the terminal 130 and/or the processing engine 140. In some embodiments, the storage 150 may store data and/or instructions that the processing engine 140 may execute or use to perform exemplary methods described in the present disclosure.

In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the imaging system 100 (e.g., the processing engine 140, the terminal 130, etc.). One or more components in the imaging system 100 may access the data or instructions stored in the storage 150 via the network 120. In some embodiments, the storage 150 may be directly connected to or communicate with one or more other components in the imaging system 100 (e.g., the processing engine 140, the terminal 130, etc.). In some embodiments, the storage 150 may be part of the processing engine 140.

FIG. 1-B is a block diagram illustrating an exemplary processing engine 140 according to some embodiments of the present disclosure. As illustrated in FIG. 1-B, the processing engine 140 may include an acquisition module 141, a control module 142, a storage module 143, a processing module 144, and a display module 145.

The acquisition module 141 may acquire or receive ECT data. Merely by way of example with reference to a PET system, the acquisition module 141 may acquire or receive PET data. For illustration purposes, during a PET scan or analysis, PET tracers (also referred to as "PET tracer molecules") are first introduced into the subject before an imaging process begins. During the PET scan, the PET tracer molecules may emit positrons, namely the antiparticles of electrons. A positron has the same mass and the opposite electrical charge compared to an electron, and it undergoes an annihilation (also referred to as an "annihilation event") with an electron (that may naturally exist in abundance within the subject) as the two particles collide. An electron-positron annihilation may result in two 511 keV gamma photons, which, upon their own generation, begin to travel in opposite directions with respect to one another. The line connecting the two gamma photons may be referred to as a line of response (LOR). The acquisition module 141 may obtain the trajectory and/or information of the gamma photons. The PET data may be used to determine a list of annihilation events, transverse and longitudinal positions of the LORs, or the like, or a combination thereof.

The control module 142 may generate a control parameter for controlling the acquisition module 141, the storage module 143, the processing module 144, and/or the display module 145. For example, the control module 142 may control the acquisition module 141 as to whether to acquire a signal, the time when a signal acquisition may occur, etc. As another example, the control module 142 may control the processing module 144 to select different algorithms to process the ECT data, acquire a motion signal (e.g., a respiratory motion signal), determine one or more symmetry related parameters of the motion signal, and/or correct the motion signal. In some embodiments, the control module 142 may receive a real-time or a predetermined command provided by a user (e.g., a doctor) or the system 100 and control the acquisition module 141, and/or the processing module 144 to acquire ECT data of a subject according to the received command. In some embodiments, the control module 142 may communicate with other modules in the processing engine 140 for exchanging information or data.

The storage module 143 may store the acquired ECT data, the control parameters, the processed ECT data, a motion signal derived from the ECT data, a parameter related to the motion signal, or the like, or a combination thereof. In some embodiments, the storage module 143 may include a mass storage, a removable storage, a volatile read-and-write memory, a read-only memory (ROM), or the like, or any combination thereof. The mass storage may include a magnetic disk, an optical disk, a solid-state drives, etc. The removable storage may include a flash drive, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage module 143 may store one or more programs and/or instructions that may be executed by one or more processors of the processing engine 140 (e.g., the processing module 144) to perform exemplary techniques described in the disclosure. For example, the storage module 143 may store program(s) and/or instruction(s) executed by the processor(s) of the processing engine 140 to acquire ECT data, acquire a respiratory motion signal via the ECT data, reconstruct an image based on the ECT data, or display any intermediate result or a resultant image.

The processing module 144 may process data received from one or more modules in the processing engine 140. In some embodiments, the processing module 144 may process the ECT data acquired by the acquisition module 141, or retrieved from the storage module 143. In some embodiments, the processing module 144 may extract a motion signal from the ECT data, reconstruct ECT images based on the ECT data, generate reports including one or more ECT images and/or other related information, determine whether the motion signal is flipped, correct the respiratory motion signal, or the like, or a combination thereof. For example, the processing module 144 may process the ECT data based on a gating approach and reconstruct an ECT image based on the gated ECT data. As another example, the processing module 144 may determine a plurality of gating parameters for the ECT data corresponding to a plurality of spatial points of the subject (e.g., chest, back, or the like) based on the motion signal.

The display module 145 may display any information related to the processing engine 140. The information may include programs, software, algorithms, data, text, number, images, voice, or the like, or any combination thereof. In some embodiments, the display module 145 may include a liquid crystal display (LCD), a light emitting diode (LED) based display, a flat panel display, a cathode ray tube (CRT), a touch screen, or the like, or a combination thereof. The touch screen may include, for example, a resistance touch screen, a capacity touch screen, a plasma touch screen, a vector pressure sensing touch screen, an infrared touch screen, or the like, or a combination thereof.

In some embodiments, one or more modules illustrated in FIG. 1-B may be implemented in at least part of the exemplary imaging system 100 illustrated in FIG. 1-A. The acquisition module 141, the control module 142, the storage module 143, the processing module 144, and/or the display module 145 may be integrated into a console. Via the console, a user may set parameters for scanning, control the imaging procedure, control a correcting procedure of a motion signal, control a parameter of the reconstruction of an image, view the motion signal, view the reconstructed images, etc. In some embodiments, the console may be implemented in the computing device as illustrated in FIG. 1-C.

FIG. 1-C is a schematic diagram illustrating an exemplary computing device 160 on which the processing engine 140 may be implemented according to some embodiments of the present disclosure.

The computing device 160 may be a general purpose computer or a special purpose computer. Both may be used to implement the processing engine 140 of the present disclosure. For example, the processing engine 140 of the imaging system 100 may be implemented on the computing device 160, via its hardware, software program, firmware, or a combination thereof. Although only one such computer is shown for convenience, the computer functions related to the imaging system 100 as described herein may be implemented in a distributed manner on a number of similar platforms to distribute the processing load.

The computing device 160, for example, may include communication (COMM) ports 165 connected to and from a network (e.g., the network 120) connected thereto to facilitate data communications. The computing device 160 may also include a processor (e.g., a central processing unit (CPU)) 162, in the form of one or more processors, for executing program instructions. The exemplary computer platform may include an internal communication bus 161, program storage and data storage of different forms, for example, a disk 167, and a read only memory (ROM) 163, or a random access memory (RAM) 164, for various data files to be processed and/or transmitted by the computer. The exemplary computer platform may also include program instructions stored in the ROM 163, the RAM 164, and/or other type of non-transitory storage medium to be executed by the processor 162. The methods and/or processes of the present disclosure may be implemented as the program instructions. The computing device 160 also includes an I/O component 166, supporting input/output between the computer and other components therein. The computing device 160 may also receive programming and data via network communications.

Merely for illustration, only one processor is described in the computing device 160. However, it should be noted that the computing device 160 in the present disclosure may also include multiple processors, and thus operations that are performed by one processor as described in the present disclosure may also be jointly or separately performed by the multiple processors. For example, the processor of the computing device 160 executes both operation A and operation B. As in another example, operation A and operation B may also be performed by two different processors jointly or separately in the computing device 160 (e.g., the first processor executes operation A and the second processor executes operation B, or the first and second processors jointly execute operations A and B).

FIG. 1-D is a schematic diagram illustrating exemplary hardware and/or software components of an exemplary mobile device 170 on which the terminal 130 may be implemented according to some embodiments of the present disclosure. As illustrated in FIG. 1-D, the mobile device 170 may include a communication platform 171, a display 172, a graphic processing unit (GPU) 173, a central processing unit (CPU) 174, an I/O 175, a memory 176, and a storage 179. In some embodiments, any other suitable component, including but not limited to a system bus or a controller (not shown), may also be included in the mobile device 170. In some embodiments, a mobile operating system 177 (e.g., iOS™, Android™ Windows Phone™, etc.) and one or more applications 178 may be loaded into the memory 176 from the storage 179 in order to be executed by the CPU 174. The applications 178 may include a browser or any other suitable mobile apps for receiving and rendering information relating to image processing or other information from the processing engine 140. User interactions with the information stream may be achieved via the I/O 175 and provided to the processing engine 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

FIG. 2 is a block diagram illustrating an exemplary processing module 144 according to some embodiments of the present disclosure. The processing module 144 may include a motion signal acquisition unit 202, a symmetry determination unit 204, a flip determination unit 206, and a correction unit 208. In some embodiments, the units may be connected with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or a combination thereof). The processing module 144 may be implemented on various components (e.g., the processor 162 of the computing device 160 as illustrated in FIG. 1-C). For example, at least a portion of the processing module 144 may be implemented on the computing device 160 as illustrated in FIG. 1-C or the mobile device 170 as illustrated in FIG. 1-D.

The motion signal acquisition unit 202 may acquire a motion signal. The motion signal may reflect a motion state of a subject. For example, a respiratory motion signal may reflect the motion of a tissue or an organ that is influenced by the respiratory motion of a subject. A cardiac motion signal may reflect the motion of the heart of a subject.

In some embodiments, the motion signal acquisition unit 202 may acquire the motion signal through an external device that detects a motion of the subject or a portion of the subject. In some embodiments, the motion signal acquisition unit 202 may acquire the motion signal based on ECT data generated from a subject or a portion of the subject. For example, the motion signal acquisition unit 202 may extract the respiratory motion signal from ECT data based on a data-driven technique. Exemplary data-driven techniques may include an approach based on a center of mass, an approach based on counts levels, an approach of a principal component analysis, or the like, or any combination thereof. The motion signal acquisition unit 202 may acquire the respiratory motion signal during or after the scanning, and/or before image reconstruction.

Figure 11:
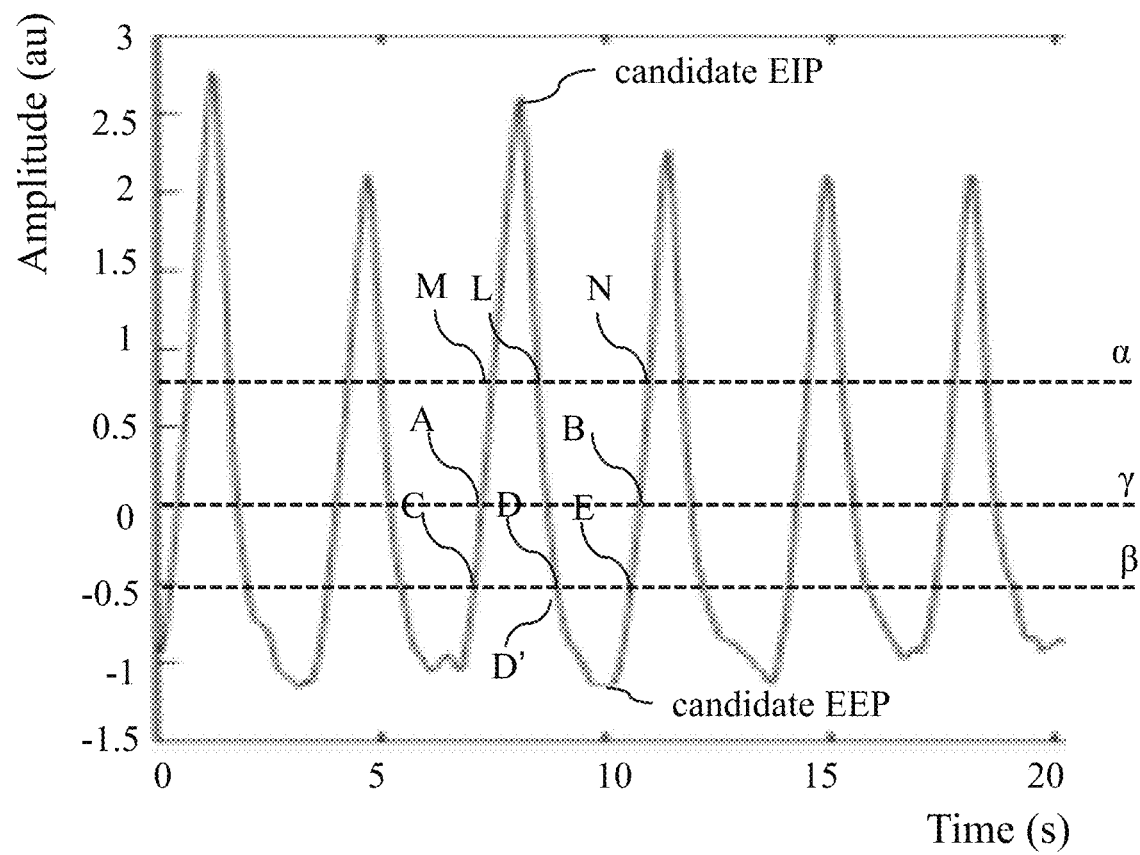
FIG. 11 illustrates an exemplary respiratory motion signal according to some embodiments of the present disclosure.

The symmetry determination unit 204 may determine one or more values of a symmetry related parameter of a motion signal. For illustration purposes, a respiratory motion signal, as shown in FIG. 11, is taken as an example. As shown in FIG. 11, the amplitude of the respiratory motion signal changes over time. In some embodiments, the amplitude of the respiratory motion signal may correspond to the displacement of a portion of an organ along a specific direction, e.g., the direction perpendicular to the coronal plane of a subject (e.g., a patient). In some embodiments, an ascending phase in the respiratory motion signal may be referred to as a candidate inspiration phase, and a descending phase in the respiratory motion signal may also be referred to as a candidate expiration phase. In some embodiments, the symmetry related parameter may be determined based on the asymmetry between the transition from an ascending phase to a descending phase and the transition from a descending phase to an ascending phase. For example, the transition from the ascending phase to the descending phase appears sharper than the transition from the descending phase to the ascending phase in the respiratory motion signal as shown in FIG. 11. With respect to a respiratory motion signal, the value of a symmetry related parameter may include an off-center value of the respiratory motion signal. The determination of the value of the symmetry related parameter may be found elsewhere in the disclosure. See, e.g., FIG. 4 and the description thereof.

The flip determination unit 206 may determine whether a motion signal is flipped. It should be noted to persons having ordinary skills in the art that a motion signal with respect to a subject may be asynchronous to the actual motion state of the subject. For illustration purposes, if a respiratory motion signal, e.g., as illustrated in FIG. 11, is flipped, an ascending phase of the respiratory motion signal may correspond to an expiration phase of the actual motion state and a descending phase may correspond to an inspiration phase of the actual motion state.

In some embodiments, the flip determination unit 206 may determine whether a respiratory motion signal is flipped based on one or more values of a symmetry related parameter. For example, the flip determination unit 206 may compare the one or more values of the symmetry related parameter with a predetermined threshold. The flip determination unit 206 may determine whether the respiratory motion signal is flipped based on the comparison.

Additionally or alternatively, the flip determination unit 206 may determine whether the respiratory motion signal is flipped based on a plurality of images. Each of the images may be reconstructed based on ECT data acquired at a time point or within a time frame. For example, the flip determination unit 206 may determine the motion of a point of interest in a plurality of images. The flip determination unit 206 may further determine whether the respiratory motion signal is flipped based on the motion of the point of interest.

The correction unit 208 may correct a motion signal. In some embodiments, the correction unit 208 may flip a respiratory motion signal if the respiratory motion signal is flipped. For example, the correction unit 208 may turn the respiratory motion signal upside down according to the reference line. Therefore, an ascending phase of the corrected respiratory motion signal may correspond to an inspiration phase of the actual motion state and a descending phase of the corrected respiratory motion signal may correspond to an expiration phase of the actual motion state.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, each of the units in the processing module 144 may access to a storage medium of the processing engine 140, or a storage medium external to the processing engine 140. As another example, the units may be partially integrated into one or more independent units or share one or more sub-units.

Figure 3:
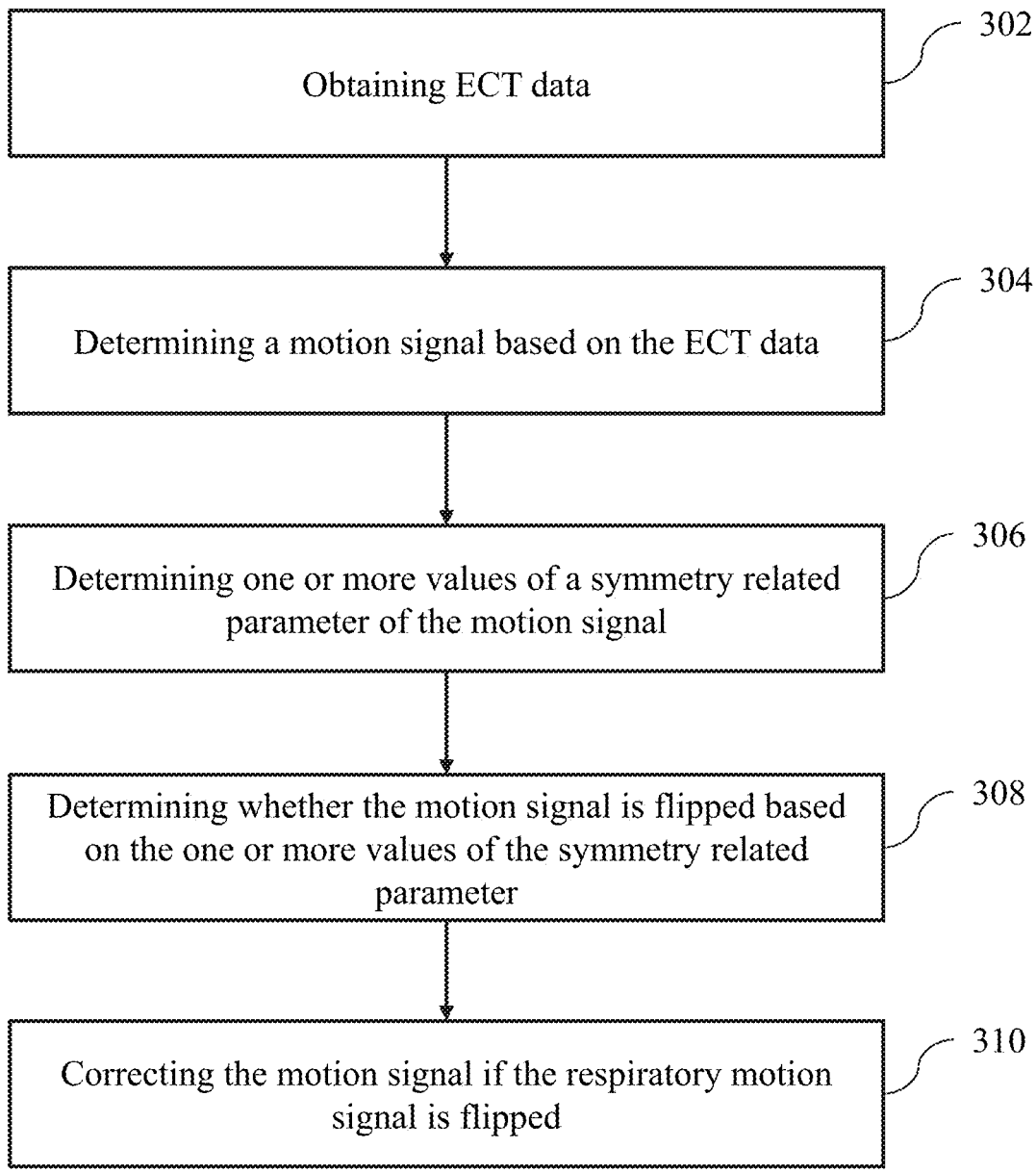
FIG. 3 is a flowchart illustrating an exemplary process for correcting a motion signal according to some embodiments of the present disclosure.

FIG. 3 is a flowchart illustrating an exemplary process for correcting a motion signal according to some embodiments of the present disclosure. The operations of the process 300 presented herein are intended to be illustrative. In some embodiments, the process 300 may be accomplished with one or more additional operations not described, and/or without one or more of the operations discussed. Additionally, the order in which the operations of the process as illustrated in FIG. 3 and described below in not intended to be limiting. In some embodiments, one or more operations of process 300 illustrated in FIG. 3 for correcting a motion signal may be implemented in the imaging system 100 illustrated in FIG. 1-A. For example, the process 300 illustrated in FIG. 3 may be stored in a storage (e.g., the storage 150) in the form of instructions, and invoked and/or executed by the processing engine 140 (e.g., the processor 162 of the computing device 160 as illustrated in FIG. 1-C, the GPU 173 or CPU 174 of the mobile device 170 as illustrated in FIG. 1-D).

In 302, ECT data may be obtained. In some embodiments, the ECT data may be obtained by the acquisition module 141. The acquisition module 141 may acquire the ECT data when the ECT scanner 110 scans a subject or a portion of the subject. For example, the ECT data may include coincidence events originating from a volume of interest (VOI) of a patient that undergoes a respiratory motion.

In 304, a motion signal may be determined based on the ECT data. In some embodiments, the motion signal may be determined by the motion signal acquisition unit 202. The motion signal may be determined based on the ECT data via various techniques. For example, a coincidence counts versus time curve may be determined, thus providing an estimated respiratory motion signal. As another example, a center of mass of, for example, a distribution of PET tracers inside a VOI may be derived from the ECT data. Then, a displacement of the center of mass as a function of time may provide a respiratory motion signal. As a further example, a principal component analysis (PCA) may be applied to the listmode ECT data. Then, a respiratory motion signal may be obtained as the principal component weight factor whose frequency spectrum has the highest peak among the frequency band of a respiratory motion.

The motion signal acquisition unit 202 may acquire the respiratory motion signal during or after the scanning, and/or before an image reconstruction process. Exemplary respiratory motion signals acquired by the respiratory motion signal acquisition unit 202 may be found elsewhere in the present disclosure. See, e.g., FIG. 11.

In 306, one or more values of a symmetry related parameter of the motion signal may be determined. In some embodiments, the one or more values of the symmetry related parameter may be determined by the symmetry determination unit 204. For illustration purpose, the values of the symmetry related parameter of a respiratory motion signal may correspond to an asymmetry between a transition from a candidate inspiration phase to a candidate expiration phase and a transition from a candidate expiration phase to a candidate inspiration phase in one or more respiratory cycles.

In some embodiments, the value(s) of the symmetry related parameter may be determined based on an end of a candidate inspiration phase (also referred as a candidate EIP) and/or an end of a candidate expiration phase (also referred as a candidate EEP). As used herein, a candidate EIP may refer to an end of an ascending phase in the respiratory motion signal, such as a crest of the respiratory motion signal as illustrated in FIG. 11. As used herein, a candidate EEP may refer to an end of a descending phase in the respiratory motion signal, such as a trough in the respiratory motion signal as illustrated in FIG. 11.

A candidate EIP may be identified by determining a local maximum motion amplitude (or referred to as a local maximum for brevity) on the respiratory motion signal. A candidate EEP may be identified by determining a local minimum motion amplitude (or referred to as a local minimum for brevity) on the respiratory motion signal.

In some embodiments, the value(s) of the symmetry related parameter may be determined based on a duration of the transition from a candidate inspiration phase to a candidate expiration phase (also referred to as "first transition") and/or a duration of the transition from a candidate expiration phase to a candidate inspiration phase (also referred to as "second transition"). The duration of the first transition or the second transition may be determined with respect to a reference line, e.g., line α, β, or γ as illustrated in FIG. 11. Details regarding the reference line may be found elsewhere in the disclosure.

In some embodiments, the value(s) of the symmetry related parameter may be determined according to one respiratory cycle (e.g., the respiratory cycle located between point A and point B as illustrated in FIG. 11). In some embodiments, a respiratory motion signal with a duration of time that is greater than a threshold, e.g., 100 seconds, may be used to determine the value(s) of the symmetry related parameter. Multiple values of the symmetry related parameter may be determined according to different portions of the respiratory motion signal. For example, the different portions of the respiratory motion signal may include a same time interval. As another example, two different portions of the respiratory motion signal used to determine the value(s) of the symmetry related parameter do not overlap. As a further example, two different portions of the respiratory motion signal may at least partially overlap. For instance, the different portions of the respiratory motion signal may have a same starting time point or different start time points, and a same end time point or different end time points.

In 308, whether the motion signal is flipped may be determined based on the one or more values of the symmetry related parameter. In some embodiments, whether the motion signal is flipped may be determined by the flip determination unit 206. In some embodiments, a respiratory motion signal may be deemed flipped if a candidate EIP and a candidate EEP in the respiratory motion signal are flipped. In some embodiments, a respiratory motion signal may be deemed flipped if an ascending phase in the respiratory motion signal and a descending phase in the respiratory motion signal are flipped.

One or more conditions may be used in determining whether the respiratory motion signal is flipped. For example, the one or more conditions may including comparing the one or more values of the symmetry related parameter with a predetermined threshold. Alternatively or additionally, the one or more conditions may include determining credibility of the one or more values of the symmetry related parameter, and then determining whether the respiratory motion signal is flipped based on the credibility of the one or more values of the symmetry related parameter.

In 310, the motion signal may be corrected if the motion signal is flipped. In some embodiments, the correction of the respiratory motion signal may be performed by the correction unit 208. In some embodiments, the correction of the respiratory motion signal may include flipping the respiratory motion signal, e.g., flipping the respiratory motion signal upside down. In some embodiments, "the respiratory motion signal is flipped" may refer to that every respiratory cycle, including a candidate EIP and a candidate EEP, is flipped. In some embodiments, "the respiratory motion signal is flipped" may refer to that part of the respiratory motion signal, including some of the respiratory cycles, are flipped.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, operation 302 may be omitted, and thus the motion signal may be acquired by a device, e.g., a sensor. For example, a sensor (e.g., a pressure sensor, a motion sensor) may be used to collect data related to the displacement of the chest or abdominal wall of a subject. Based on the data collected by the sensor, the motion signal acquisition unit 202 may derive a respiratory motion signal with respect to the subject.

Figure 4:
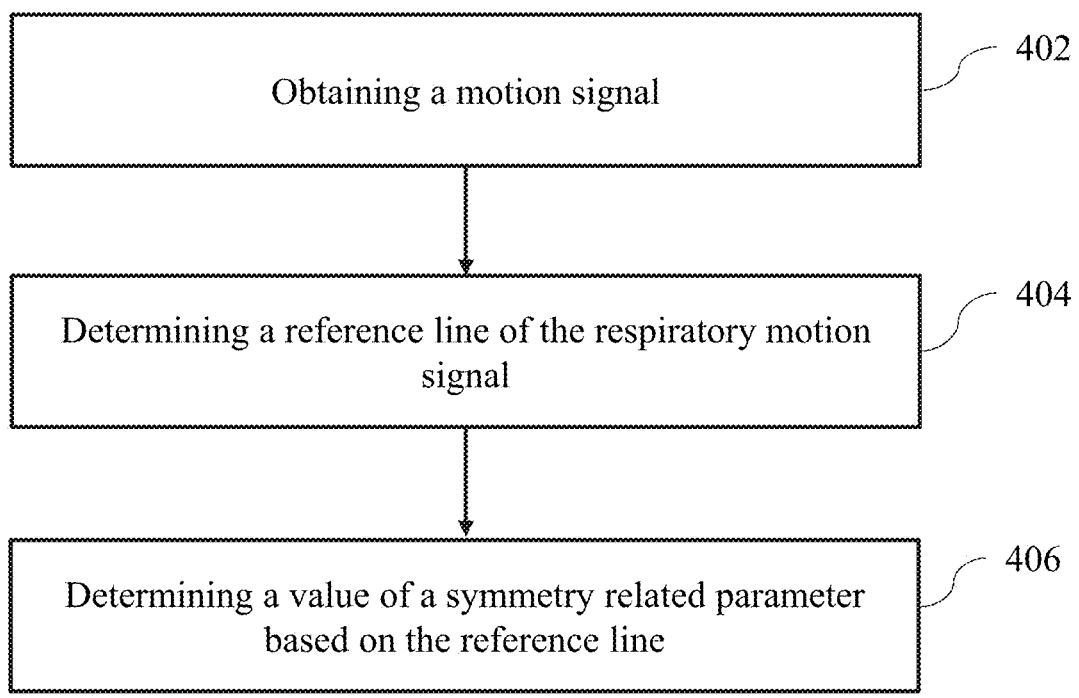
FIG. 4 is a flowchart illustrating an exemplary process for determining one or more values of a symmetry related parameter of a motion signal according to some embodiments of the present disclosure.

FIG. 4 is a flowchart illustrating an exemplary process for determining one or more values of a symmetry related parameter of a motion signal according to some embodiments of the present disclosure. In some embodiments, the process 400 may be performed to achieve 306 as illustrated in FIG. 3. The operations of the process 400 presented herein are intended to be illustrative. In some embodiments, the process 400 may be accomplished with one or more additional operations not described, and/or without one or more of the operations discussed. Additionally, the order in which the operations of the process as illustrated in FIG. 4 and described below in not intended to be limiting. In some embodiments, one or more operations of process 400 illustrated in FIG. 4 for determining one or more symmetry related parameters of a motion signal may be implemented in the imaging system 100 illustrated in FIG. 1-A. For example, the process 400 illustrated in FIG. 4 may be stored in a storage (e.g., the storage 150) in the form of instructions, and invoked and/or executed by the processing engine 140 (e.g., the processor 162 of the computing device 160 as illustrated in FIG. 1-C, the GPU 173 or CPU 174 of the mobile device 170 as illustrated in FIG. 1-D).

In 402, a motion signal may be obtained. In some embodiments, the motion signal may be acquired by the motion signal acquisition unit 202 as described elsewhere in the present disclosure.

In 404, a reference line of the motion signal may be determined. In some embodiments, the determination of the reference line of the respiratory motion signal may be performed by the symmetry determination unit 204. The reference line may separate the motion signal into two parts, a first part above the reference line and a second part below the reference line. In some exemplary embodiments with respect to a respiratory motion signal, one or more candidate EIPs may be located above the reference line, and one or more candidate EEPs may be located below the reference line. It should be appreciated that if the respiratory motion signal is not flipped, the candidate EIPs/EEPs may be deemed as actual EIPs/EEPs with respect to the actual motion of a subject. If the respiratory motion signal is flipped, the candidate EIPs may correspond to actual EEPs, the candidate EEPs may correspond to actual EIPs, and thus the respiratory motion signal may need to be corrected.

In some embodiments, the reference line may be determined based on an amplitude of a candidate EIP and an amplitude of a candidate EEP. As used herein, an amplitude of a candidate EIP may be a first peak amplitude of the respiratory motion signal with respect to the reference line, and an amplitude of a candidate EEP may be a first valley amplitude of the respiratory motion signal with respect to the reference line. For example, the reference line may be midway between the candidate EIP and the candidate EEP such that the amplitude of the candidate EIP is equal to the amplitude of the candidate EEP. Referring to FIG. 11 as an example, the reference line may be line α. The candidate EIP and candidate EEP between point M and point N may have a same amplitude with respect to the line α. Points M and N are where the motion signal intersects with the reference line α, and the motion signal between M and N spans at least one cycle of the respiratory motion of interest. In some embodiments, the candidate EIP and the candidate EEP used to determine the reference line may occur within the same cycle or in different cycles of the respiratory motion. In some embodiments, the first peak amplitude of the respiratory motion signal with respect to the reference line may be an average peak amplitude of a plurality peaks in the respiratory motion signal. The first valley amplitude of the respiratory motion signal with respect to the reference line may be an average valley amplitude of a plurality valleys in the respiratory motion signal.

In some embodiments, the reference line may be determined based on a duration of a first transition of a respiratory motion signal and a duration of a second transition of the respiratory motion signal. The duration of the first transition may refer to a time period including part of a candidate inspiration phase before a candidate EIP and part of a candidate expiration phase after the candidate EIP. The duration of the second transition may refer to a time period including part of a candidate expiration phase before a candidate EEP and part of a candidate inspiration phase after the candidate EEP. For example, the reference line may be determined such that the duration of the first transition is equal to the duration of the second transition. With reference to the reference line, the duration of the first transition may refer to a time period including part of a candidate inspiration phase before a candidate EIP and part of a candidate expiration phase after the candidate EIP, in which both parts are above the reference line as illustrated in FIG. 11; the duration of the second transition may refer to a time period including part of a candidate expiration phase before a candidate EEP and part of a candidate inspiration phase after the candidate EEP, in which both parts are below the reference line as illustrated in FIG. 11. Referring to FIG. 11 as an example, the reference line may be line β. The duration of the first transition, represented by the interval between point C and point D, is equal to the duration of the second transition, represented by the interval between point D' and point E. Points C, D, D', and E are where the motion signal intersects with the reference line β. In some embodiments, the duration of the first transition and the duration of the second transition used to determine the reference line may occur in a same cycle of the respiratory motion; D and D' may coincide with each other. In some embodiments, the duration of the first transition and the duration of the second transition used to determine the reference line may occur in different cycles of the respiratory motion; D and D' are separate from each other.

In some embodiments, the reference line may be determined based on a first criterion including a combination of an amplitude and a duration of a respiratory motion signal or part of the respiratory motion signal. For example, the first criterion may refer to that the area above the reference line (e.g., represented by an integration of the first part of the respiratory motion signal above the reference line) is equal to the area below the reference line (e.g., represented by an integration of the second part of the respiratory motion signal below the reference line). For illustration purposes, the motion amplitude corresponding to the reference line may be determined as follows:

$$R_\gamma = \frac{\int_{t_1}^{t_2} s(t)dt}{t_2 - t_1}, \quad (1)$$

where $R_\gamma$ is the motion amplitude corresponding to the reference line, $t_1$ is a first time point of the respiratory motion signal, $t_2$ is a second time point of the respiratory motion signal, s(t) is the respiratory motion signal acquired according to some embodiments of the present disclosure. The first time point may be the starting point of the respiratory motion signal. The second time point may be any time point, other than the first time point, of the respiratory motion signal. In some embodiments, the interval between the first time point and the second time point may be no less than a threshold, such as 100 seconds.

In 406, a value of a symmetry related parameter may be determined based on the reference line. In some embodiments, the determination of the value of the symmetry related parameter based on the reference line may be performed by the symmetry determination unit 204.

In some embodiments with respect to a respiratory motion signal, the value of the symmetry related parameter may be determined in different manners if the reference line is determined in different manners.

Merely by way of example, if the reference line is determined on the basis that an amplitude of a candidate EIP is equal to an amplitude of a candidate EEP, the value of the symmetry related parameter may be determined based on the duration of a first transition related to the candidate EIP and the duration of a second transition related to the candidate EEP. As described elsewhere in the present disclosure, with reference to the reference line, the duration of the first transition may refer to a time period including part of a candidate inspiration phase before a candidate EIP and part of a candidate expiration phase after the candidate EIP, in which both parts are above the reference line as illustrated in FIG. 11; the duration of the second transition may refer to a time period including part of a candidate expiration phase before a candidate EEP and part of a candidate inspiration phase after the candidate EEP, in which both parts are below the reference line as illustrated in FIG. 11. Then, the value of the symmetry related parameter D may be determined based on the following formula:

$$D = \frac{T_1}{T_2}, \quad (2)$$

where $T_1$ is the duration of the first transition related to the candidate EIP, and $T_2$ is the duration of the second transition related to the candidate EEP.

Referring to FIG. 11 as an example, the reference line may be the line α. The duration of the first transition related to the candidate EIP may be represented by the interval between point M and point L. The duration of the second transition related to the candidate EEP may be represented by the interval between point L and point N. Points L, M, and N are where the motion signal intersects with the reference line α as illustrated in FIG. 11.

Merely by way of example, if the reference line is determined on the basis that a duration of a first transition is equal to a duration of a second transition, the value of the symmetry related parameter may be determined based on an amplitude of one or more candidate EIPs related to the first transition and/or an amplitude of one or more candidate EEPs related to the second transition. In some embodiments, the one or more candidate EIPs related to the first transition may be identified at a local maximum during the first transition. The one or more candidate EEPs related to the second transition may be identified at a local minimum during the second transition. In some embodiments, the amplitude of one or more candidate EIPs may be an average peak amplitude of the one or more candidate EIPs of the motion signal with respect to the reference line. The amplitude of one or more candidate EEPs may be an average valley amplitude of the one or more candidate EEPs of the motion signal with respect to the reference line. Then, the value of the symmetry related parameter D may be determined based on the following formula:

$$D = \frac{H_{max}}{H_{min}}, \quad (3)$$

where $H_{max}$ is the amplitude of one or more candidate EIPs related to the first transition with respect to the reference line, and $H_{min}$ is the amplitude of one or more candidate EEPs with respect to the second transition with respect to the reference line.

Merely by way of example, if the reference line is determined based on the first criterion as described according to formula (1), the value of the symmetry related parameter may be determined based on a second criterion that includes a combination of a weighted amplitude and a duration of the respiratory motion signal or part of the respiratory motion signal. For illustration purposes, the value of the symmetry related parameter D in accordance to the second specific criterion may be determined as follows:

$$s_2(t) = s(t) - R_\gamma, \quad (4)$$

$$D = \frac{\int_{t_1}^{t_2} s_2(t)f(|s_2(t)|)dt}{t_2 - t_1}, \quad (5)$$

where $t_1$ and $t_2$ are the first and second time points as illustrated in formula (1), s(t) is the respiratory motion signal that is acquired according to some embodiments of the present disclosure, $s_2(t)$ is a second respiratory motion signal that is determined based on the respiratory signal s(t) and the reference line $R_\gamma$ (the reference line acquired according to the first criteria), $|s_2(t)|$ is the absolute value of the second respiratory motion signal, and f( ) is a mono-increase function. It shall be noted that the value of the symmetry related parameter D may indicate which part of the respiratory motion signal, the part above the reference line or the part below the reference line, appears sharper. In some embodiments, if the part above the reference line appears sharper than the part below the reference line, the value of the symmetry related parameter D may be positive. Likewise, if the part below the reference line appears sharper than the part above the reference line, the value of the symmetry related parameter D may be negative.

The mono-increase function may include a polynomial function, an exponential function, a logarithmic function, or the like, or a combination thereof. For example, f( ) may be a polynomial, such as f( )=x². Accordingly, the formula (5) may be converted to:

$$D = \frac{\int_{t_1}^{t_2} (s_2(t))^3 dt}{t_2 - t_1}. \tag{6}$$

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, only one symmetry related parameter may be determined based on one reference line. In some embodiments, more than one symmetry related parameters may be determined based on one reference line.

Figure 5:
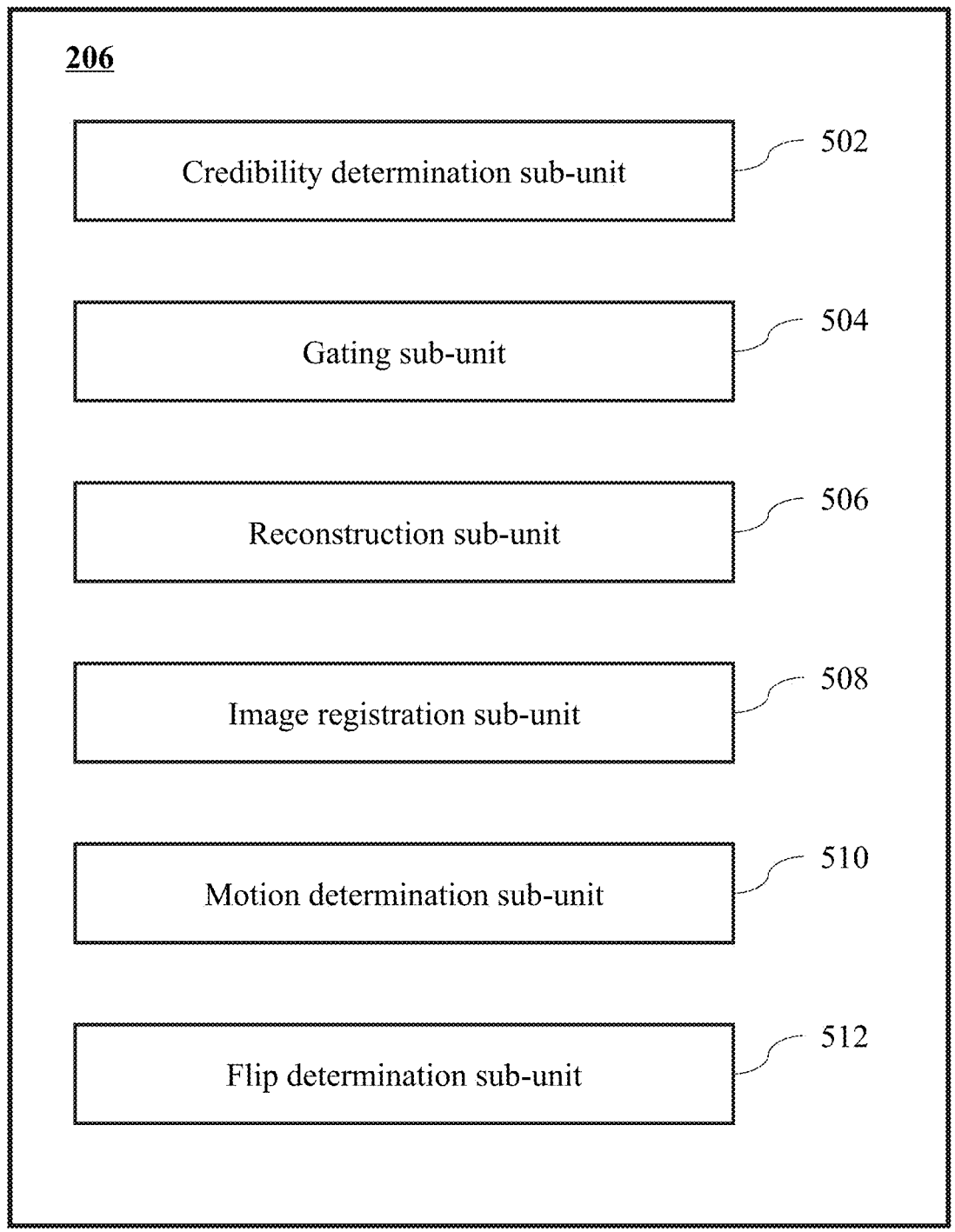
FIG. 5 is a block diagram illustrating an exemplary flip determination unit according to some embodiments of the present disclosure.

FIG. 5 is a block diagram illustrating an exemplary flip determination unit 206 according to some embodiments of the present disclosure. The flip determination unit 206 may include a credibility determination sub-unit 502, a gating sub-unit 504, a reconstruction sub-unit 506, an image registration sub-unit 508, a motion determination sub-unit 510, and a flip determination sub-unit 512. The flip determination unit 206 may be implemented on various components (e.g., the processor 162 of the computing device 160 as illustrated in FIG. 1-C). For example, at least a portion of the flip determination unit 206 may be implemented on the computing device 160 as illustrated in FIG. 1-C or the mobile device 170 as illustrated in FIG. 1-D.

The credibility determination sub-unit 502 may determine the credibility of one or more values of a symmetry related parameter of a motion signal. The credibility of the one or more values of the symmetry related parameter may be determined according to various conditions, including a duration of the motion signal, a value(s) of the symmetry related parameter, the noise with respect to the motion signal, or the like, or a combination thereof. Details regarding the credibility of the value(s) of the symmetry related parameter may be found elsewhere in the present disclosure. See, for example, FIG. 9 and the description thereof.

The gating sub-unit 504 may gate ECT data related to a subject. As used herein, "gating" may refer to the operation in which ECT data may be classified into a plurality of frames (also referred to as "gated data") corresponding to a plurality of time intervals or motion phases. For example, the ECT data may be gated based on the motion phases of a respiratory motion signal derived from the ECT data. The gating sub-unit 504 may divide the respiratory motion signal into a plurality of sections or phases. Each of the plurality of sections or phases may correspond to a same frame of gate ECT data.

Merely by way of example, the ECT data may be divided into two frames. One of the frames may correspond to, for example, the first part of a respiratory motion signal that is above a reference line. The other frame may correspond to, for example, the second part of the respiratory motion signal that is below the reference line. In some embodiments, the gated data may be processed to reconstruct images corresponding to different time intervals that relate to a motion of a subject.

The reconstruction sub-unit 506 may reconstruct an image. In some embodiments, the reconstruction sub-unit 506 may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or a combination thereof. In some embodiments, the reconstruction sub-unit 506 may use different reconstruction algorithms including an analytic reconstruction algorithm or an iterative reconstruction algorithm for image reconstruction.

Exemplary analytic reconstruction algorithms may include a filter back projection (FBP) algorithm, a back projection filter (BFP) algorithm, a p-filtered layer gram, or the like, or a combination thereof. Exemplary iterative reconstruction algorithms may include a Maximum Likelihood Expectation Maximization (ML-EM), an Ordered Subset Expectation Maximization (OSEM), a Row-Action Maximum Likelihood Algorithm (RAMLA), a Dynamic Row-Action Maximum Likelihood Algorithm (DRAMA), or the like, or a combination thereof. In some embodiments, the reconstruction sub-unit 506 may reconstruct images based on the gated ECT data generated by the gating sub-unit 504.

The image registration sub-unit 508 may perform an image registration of a plurality of images. In some embodiments, the image registration sub-unit 508 may perform a registration of two or more images in a direction, e.g., in the z direction. As used herein, the z direction may represent a direction that is perpendicular to the transverse plane of a subject (i.e., the direction from head to feet of a patient).

The motion determination sub-unit 510 may determine a motion trend of a subject. In some embodiments, the motion determination sub-unit 510 may determine the motion trend of the subject by determining the motion of a point of interest within the subject. For example, the motion of the point of interest along a specific direction (e.g., the z direction) may be determined to represent the motion trend of the subject. In some embodiments, the motion trend of the subject may be determined based on a registration of two images of the subject corresponding to different time intervals.

The flip determination sub-unit 512 may determine whether a motion signal is flipped. In some embodiments, the flip determination sub-unit 512 may determine whether a respiratory motion signal is flipped based on one or more values of a symmetry related parameter with respect to the respiratory motion signal. In some embodiments, the flip determination sub-unit 512 may determine whether a respiratory motion signal is flipped based on the motion trend of a subject, details of which may be found elsewhere in the disclosure.

It should be noted that the above description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, each of the sub-units in the flip determination unit 206 may access to a storage medium of the processing engine 140, or a storage medium external to the processing engine 140. As another example, the sub-units may be partially integrated into one or more independent sub-units or share one or more blocks.

Figure 6:
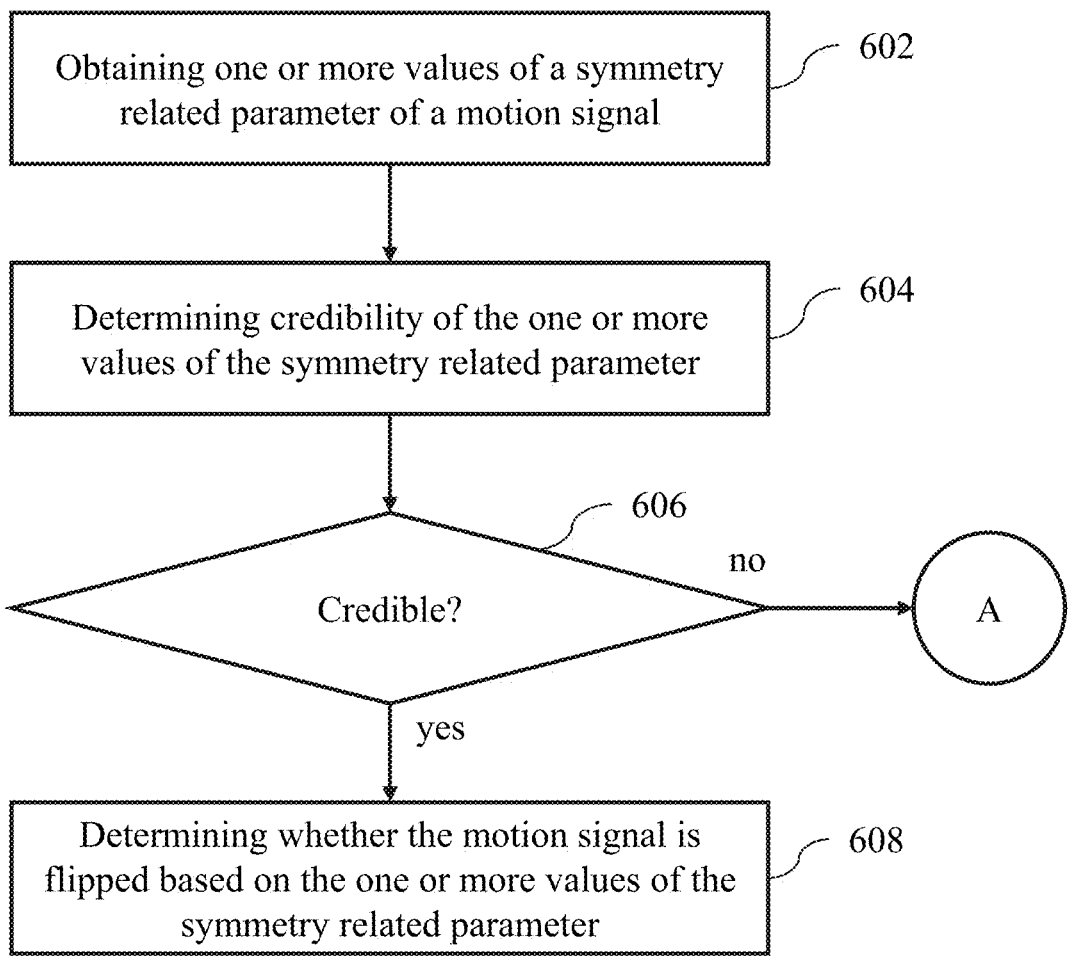
FIG. 6 is a flowchart illustrating an exemplary process for determining whether a respiratory motion signal is flipped according to some embodiments of the present disclosure.

FIG. 6 is a flowchart illustrating an exemplary process for determining whether a respiratory motion signal is flipped according to some embodiments of the present disclosure. In some embodiments, the process 600 may be performed to achieve 308 as illustrated in FIG. 3. The operations of the process 600 presented herein are intended to be illustrative. In some embodiments, the process 600 may be accomplished with one or more additional operations not described, and/or without one or more of the operations discussed. Additionally, the order in which the operations of the process as illustrated in FIG. 6 and described below in not intended to be limiting. In some embodiments, one or more operations of process 600 illustrated in FIG. 6 for determining whether a respiratory motion signal is flipped may be implemented in the imaging system 100 illustrated in FIG. 1-A. For example, the process 600 illustrated in FIG. 6 may be stored in a storage (e.g., the storage 150) in the form of instructions, and invoked and/or executed by the processing engine 140 (e.g., the processor 162 of the computing device 160 as illustrated in FIG. 1-C, the GPU 173 or CPU 174 of the mobile device 170 as illustrated in FIG. 1-D).

In 602, one or more values of a symmetry related parameter of a motion signal may be obtained. In some embodiments, the one or more values of the symmetry related parameter of the motion signal may be determined by the symmetry determination unit 204 as described elsewhere in the disclosure.

In 604, a credibility of the one or more values of the symmetry related parameter may be determined. In some embodiments, the credibility of the one or more values of the symmetry related parameter may be determined by the credibility determination sub-unit 502. The credibility of the one or more values of the symmetry related parameter may be determined according to various conditions, including a duration of the motion signal, value(s) of the symmetry related parameter, a noise with respect to the motion signal, or the like, or a combination thereof. Details regarding determination of the credibility of the one or more values of the symmetry related parameter may be found elsewhere in the disclosure. See, e.g., FIG. 10 and the description thereof.

In 606, if the one or more values of the symmetry related parameter are determined as credible, the process 600 may proceed to 608. If the one or more values of the symmetry related parameter are determined as incredible, the process 600 may proceed to Node A. Description regarding Node A may be found in, for example, FIG. 7.

In 608, whether the motion signal is flipped may be determined based on the one or more values of the symmetry related parameter. In some embodiments, the determination of whether the motion signal is flipped may be performed by the flip determination sub-unit 512. In some embodiments, the determination as to whether the motion signal is flipped based on the one or more values of the symmetry related parameter may include comparing the one or more values of the symmetry related parameter with a threshold, and determining whether the motion signal is flipped based on the comparison. The threshold may be determined by the symmetry determination unit 204, or may be determined by a user through the control module 142.

In some embodiments, the determination of whether a respiratory motion signal is flipped may be based on an observation that a respiratory motion signal is asymmetric. For instance, the transition of a respiratory motion signal related to an actual EIP appears sharper than the transition of the respiratory motion signal related to an actual EEP. See, e.g., FIG. 11.

Merely by way of example with respect to the respiratory motion as described in connection with FIG. 4, if a value of the symmetry related parameter as illustrated in formula (2) is greater than 1 (i.e., D>1), it may indicate that the first transition related to the candidate EIP is sharper than the second transition related to the candidate EEP. Therefore, the actual EIP may correspond to the candidate EIP. Otherwise, if a value of the symmetry related parameter as illustrated in formula (2) is less than 1 (i.e., D<1), it may indicate that the second transition related to the candidate EEP is sharper than the first transition related to the candidate EIP. Therefore, the actual EIP may be inconsistent with the candidate EIP, and thus the respiratory motion signal is determined as flipped.

Merely by way of example with respect to the respiratory motion as described in connection with FIG. 4, if a value of the symmetry related parameter as illustrated in formula (3) is greater than 1 (i.e., D>1), it may denote that the first transition related to the candidate EIP is sharper than the second transition related to the candidate EEP. Therefore, the actual EIP may be consistent with the candidate EIP. Otherwise, if a value of the symmetry related parameter as illustrated in formula (3) is less than 1 (i.e., D<1), it may denote that the second transition related to the candidate EEP is sharper than the first transition related to the candidate EIP. Therefore, the actual EIP may be inconsistent with the candidate EIP, and thus the respiratory motion signal is determined as flipped.

Merely by way of example with respect to the respiratory motion signal as described in connection with FIG. 4, if a value of the symmetry related parameter as illustrated in formula (5) is positive (i.e., D>0), it may denote that the part where the fourth respiratory motion signal is greater than zero ($s_2(t)>0$) (or the part where the respiratory motion signal s(t) is related to the candidate EIP that is above the reference line $R_y$) appears shaper than the part where the fourth respiratory motion signal is less than zero ($s_2(t)<0$) (or the part where the respiratory motion signal s(t) is related to the candidate EEP that is below the reference line $R_y$). Therefore, the actual EIP may be consistent with the candidate EIP. Otherwise, if a value of the symmetry related parameters as illustrated in formula (5) is negative (i.e., D<0), it may denote that the part where the fourth respiratory motion signal is less than zero ($s_2(t)<0$) appears shaper than the part where the fourth respiratory motion signal is greater than zero ($s_2(t)>0$). Therefore, the actual EIP may be inconsistent with the candidate EIP, and thus the respiratory motion signal is determined as flipped.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For instance, operations 604 and 606 may be omitted and the flip determination sub-unit 512 may determine whether the motion signal is flipped based on the one or more values of the symmetry related parameter directly.

Figure 7:
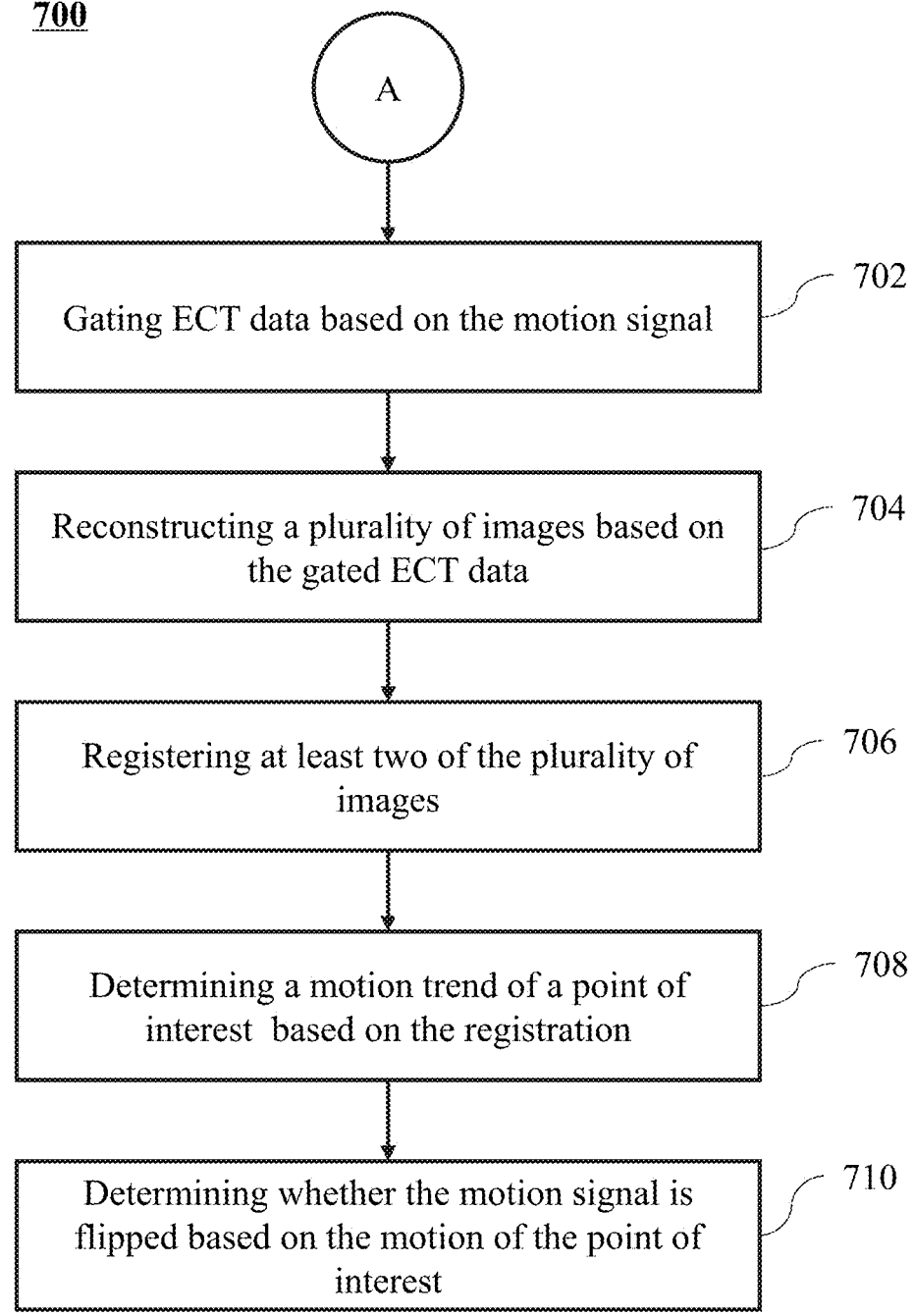
FIG. 7 is a flowchart illustrating an exemplary process of determining whether a motion signal is flipped according to some embodiments of the present disclosure.

FIG. 7 is a flowchart illustrating an exemplary process of determining whether a motion signal is flipped according to some embodiments of the present disclosure. The process 700 may be performed when the process 600 proceeds to Node A as described in FIG. 6. The operations of the process 700 presented herein are intended to be illustrative. In some embodiments, the process 700 may be accomplished with one or more additional operations not described, and/or without one or more of the operations discussed. Additionally, the order in which the operations of the process as illustrated in FIG. 7 and described below in not intended to be limiting. In some embodiments, one or more operations of process 700 illustrated in FIG. 7 for determining whether a respiratory motion signal is flipped may be implemented in the imaging system 100 illustrated in FIG. 1-A. For example, the process 700 illustrated in FIG. 7 may be stored in a storage (e.g., the storage 150) in the form of instructions, and invoked and/or executed by the processing engine 140 (e.g., the processor 162 of the computing device 160 as illustrated in FIG. 1-C, the GPU 173 or CPU 174 of the mobile device 170 as illustrated in FIG. 1-D).

In 702, ECT data may be gated based on the motion signal. The gating may be performed by the gating sub-unit 504. The gating may include dividing the ECT data into a plurality of frames, each of which may has a sequence number, such as, for example, a first frame of ECT data, a second frame of ECT data ..., a nth frame of ECT data. Each of the plurality of frames may correspond to a time interval of a section of the motion signal. The gating may be performed based on, for example, the amplitude of the motion signal, or the phase of the motion signal. Details regarding the gating of the ECT data may be found in FIG. 8 and the description thereof.

In 704, a plurality of images may be reconstructed based on the gated ECT data. In some embodiments, the reconstruction may be performed by the reconstruction sub-unit 506. One or more frames of the ECT data may be used to reconstruct an image corresponding to a motion-related state of a subject. For example, an inspiration-phase image may be reconstructed based on a frame of the ECT data in an inspiratory phase, and an expiration-phase image may be reconstructed based on a frame of the ECT data in an expiratory phase. The reconstruction sub-unit 506 may execute a reconstruction algorithm to reconstruct an image based on one or more frames of the ECT data, as described elsewhere in the present disclosure.

In 706, at least two of the plurality of images may be registered. In some embodiments, the registration of the at least two of the plurality of images may be performed by the image registration sub-unit 508. The registration of the at least two of the plurality of images may be performed to assess the difference between the at least two of the plurality of images due at least partially to the differences in motion phase of the images. Exemplary differences may include a displacement of a point of interest between two images, a deformation of a volume of interest between two images.

For illustration purposes, let F(x, y, z, g) represent a characteristic or feature of a reconstructed image, where g represents the sequence number of a frame (e.g., g=1, 2 ... n), and (x, y, z) represents the coordinate of a point (e.g., a voxel, a pixel) in the reconstructed image. As used herein, the z axis is along the z direction as described elsewhere in the disclosure, and the x axis and y axis form an x-y plane that is perpendicular to the z axis. Exemplary characteristics or features of a reconstructed image may include a gray level of a pixel/voxel, a mean gray level, a texture, a color, a contrast, a brightness, or the like, or any combination thereof. In some embodiments, the registration of the at least two of the images may be performed in a specific direction. For example, a first image reconstructed based on the first frame of the ECT data and an ith image reconstructed based on the ith frame of the ECT data (i=2, 3 ..., n) may be registered in the z direction. In some embodiments, various approaches may be used for image registration.

For example, a sum square error (SSE) based approach is used as an example in the following:

$$SSE(m(z)) = \int_{All}(F(x,y,z,i) - F(x,y,z+m(z),1))^2 dz, \quad (7)$$

where m(z) denotes a displacement vector that represents a displacement of a point represented by (x, y, z) between a first image reconstructed based on the first frame of the ECT data and ith image reconstructed based on the ith frame of the ECT data. The integration is performed based on all possible z values in the first image or the ith image.

In some embodiments, the first image and the ith image may be registered such that the deviation parameter achieves a minimum value. Therefore, the displacement vector m(z) may be determined as follows:

$$m(z) = \underset{m(z)}{\arg\min} SSE(m(z)). \quad (8)$$

Various approaches may be used to solve the equation (8). For illustration purposes, a Newton's method is described. The Newton's method include determining the displacement vector m(z) in a plurality of iterations.

Firstly, an initial value for the displacement vector m(z) is assigned. For example, the initial value of the displacement vector m(z) may be assigned as 0. Then, the gradient of the deviation parameter SSE(m(z)) is determined as:

$$g(m(z)) = \frac{d(SSE(m(z)))}{d(m(z))}, \quad (9)$$

where g(m(z)) denotes a derivative of the deviation parameter SSE(m(z)) of the displacement vector m(z), representing a sensitivity to change of the deviation parameter with respect to a change of the displacement vector.

Furthermore, a second derivative H(m(z)) of the deviation parameter SSE(m(z)) of the displacement vector m(z) is determined as:

$$H(m(z)) = \frac{dg(m(z))}{d(m(z))}. \quad (10)$$

Next, a new displacement vector $m^{new}(z)$ may be updated based on the displacement vector m(z) in the previous iteration:

$$m^{new}(z) = m(z) - \frac{g(m(z))}{H(m(z))}. \quad (11)$$

By way of iterations, the displacement vector m(z) may be updated until a termination condition is satisfied. Exemplary termination condition may include that a certain number of iterations have been performed and/or the difference between two displacement vectors determined in two successive iterations is smaller than a threshold. In some embodiments, only one iteration is performed for determining the displacement vector.

In 708, a motion of a point of interest may be determined based on the registration. In some embodiments, the motion may be determined by the motion determination sub-unit 510. The motion may refer to a direction of movement along a specific direction (e.g., the z direction) of a point of interest and/or the magnitude of the motion.

Merely by way of example, the motion of the point of interest may be determined based on the registration of the first image reconstructed based on the first frame of the ECT data and the ith image reconstructed based on the ith frame of the ECT data. A weighted displacement vector may be acquired by combining the characteristic or feature (e.g., the gray value) of the pixel/voxel with the displacement vector m(z):

$$w(z)=m(z)*F(x,y,z,1), \qquad (12)$$

where w(z) represents the weighted displacement vector.

The motion T(x, y) of at point (x, y) may be determined as follows:

$$T(x,y)=\int_{All} w(z)dz. \qquad (13)$$

In some embodiments, the point of interest may refer to the point with the largest motion (e.g., the maximum absolute value of the motion) as described below:

$$(x_m, y_m) = \underset{(x,y)}{\operatorname{argmax}} |T(x, y)|, \qquad (14)$$

where $(x_m, y_m)$ is the point of interest.

The motion T of the point of interest from the first image to the ith image may be determined as:

$$T=T(x_m,y_m). \qquad (15)$$

In some embodiments, the motion of the point of interest may be determined based on the registration of any two image, e.g., the nth image reconstructed based on the nth frame of the ECT data and the mth image reconstructed based on the mth frame of the ECT data. In some embodiments, different motions of point (x, y) may be determined based on more than one registration. The registrations may include the registration between the mth image reconstructed based the mth frame of the ECT data and the ith image reconstructed based on the ith frame of the ECT data, where m, i may denote any sequence number of a frame of the ECT data. And the different motions of point (x, y) may be combined to determine the motion of a point of interest. For example, a combination of various motions of a point may be determined as:

$$T'=\Sigma_{j=1}^{n-1} T_j)(x,y), \qquad (16)$$

where T' represents the combination of various motions of point (x, y).

In some embodiments, if the ECT data are gated based on a plurality of durations of the respiratory motion signal, as described elsewhere in the present disclosure, the motion of the point of interest in image F(x, y, z, 1) may be determined based on the registration between image F(x, y, z, 1) and image F(x, y, z, [i/2]), where [ ] used herein represents a function of rounding.

In 710, a determination may be made as to whether the motion signal is flipped based on the motion of the point of interest. In some embodiments, the determination of whether the motion signal is flipped may be performed by the flip determination sub-unit 512.

For illustration purposes, a respiratory motion signal is taken as an example. If the motion of the point of interest as shown in formula (15) is positive, it may indicate that that motion of the point of interest is along the z direction from the head to the feet of a subject. The section of a respiratory motion signal corresponding to the first frame of ECT data (also referred to as "first section of the respiratory motion signal") may be closer to an actual EIP than the section of the respiratory motion signal corresponding to the ith frame of ECT data (also referred to as "ith section of the respiratory motion signal"). If the motion of the point of interest as shown in formula (15) is negative, it may indicate that the motion of the point of interest is along the direction from the feet to the head of a patient. The ith section of the respiratory motion signal may be closer to an actual EIP than the first section of the respiratory motion signal. Then, in order to determine whether the respiratory motion signal is flipped, the position of the first section of the respiratory motion signal and the position of the ith section of the respiratory motion signal may be compared.

If the first section of the respiratory motion signal is closer to a candidate EIP than the ith section of the respiratory motion signal, the respiratory motion signal may be determined as synchronous with the actual motion phase of the subject, and thus the respiratory motion signal is determined as correct. If the ith section of the respiratory motion signal is closer to a candidate EIP than the first section of the respiratory motion signal, the respiratory motion signal may be determined as asynchronous to the actual motion phase of the subject, and thus the respiratory motion signal is determined as flipped.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the determination of whether the motion signal is flipped may be performed based on the motion trend of a point of interest between any two reconstructed images, under the condition that the sections of the motion signal with respect to the two reconstructed images are determined.

Figure 8:
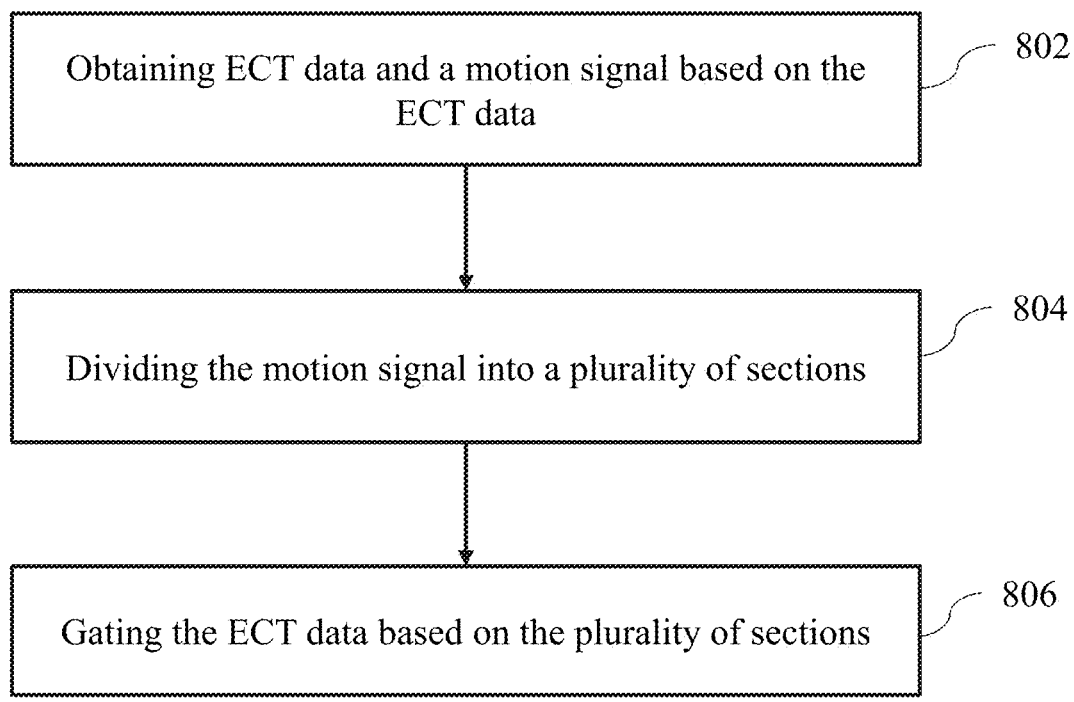
FIG. 8 is a flowchart illustrating an exemplary process for gating the ECT data according to some embodiments of the present disclosure.

FIG. 8 is a flowchart illustrating an exemplary process for gating the ECT data according to some embodiments of the present disclosure. The process 800 may be performed by the gating sub-unit 504. In some embodiments, the process 800 may be performed to achieve 702 as illustrated in FIG. 7. The operations of the process 800 presented herein are intended to be illustrative. In some embodiments, the process 800 may be accomplished with one or more additional operations not described, and/or without one or more of the operations discussed. Additionally, the order in which the operations of the process as illustrated in FIG. 8 and described below in not intended to be limiting. In some embodiments, one or more operations of process 800 illustrated in FIG. 8 for gating the ECT data may be implemented in the imaging system 100 illustrated in FIG. 1-A. For example, the process 800 illustrated in FIG. 8 may be stored in a storage (e.g., the storage 150) in the form of instructions, and invoked and/or executed by the processing engine 140 (e.g., the processor 162 of the computing device 160 as illustrated in FIG. 1-C, the GPU 173 or CPU 174 of the mobile device 170 as illustrated in FIG. 1-D).

In 802, ECT data and a motion signal based on the ECT data may be obtained. In some embodiments, the ECT data may be acquired by the acquisition module 141, and the motion signal of the ECT data may be acquired by the processing module 144, as described elsewhere in the present disclosure. In some embodiments, the ECT data and/or the motion signal of the ECT data may be retrieved from a storage device including, e.g., the storage 150, storage module 143, disk 167 and storage 179, an external storage device accessible by the system 100 or a portion thereof via, for example, the network 120, etc.

In 804, the motion signal may be divided into a plurality of sections. In some embodiments, the motion signal may be divided by the gating sub-unit 504. In some embodiments, the motion signal may be divided into a plurality of sections based on the amplitude of the motion signal, the distribution of coincidence events, or the motion phases of the motion signal.

Figure 12:
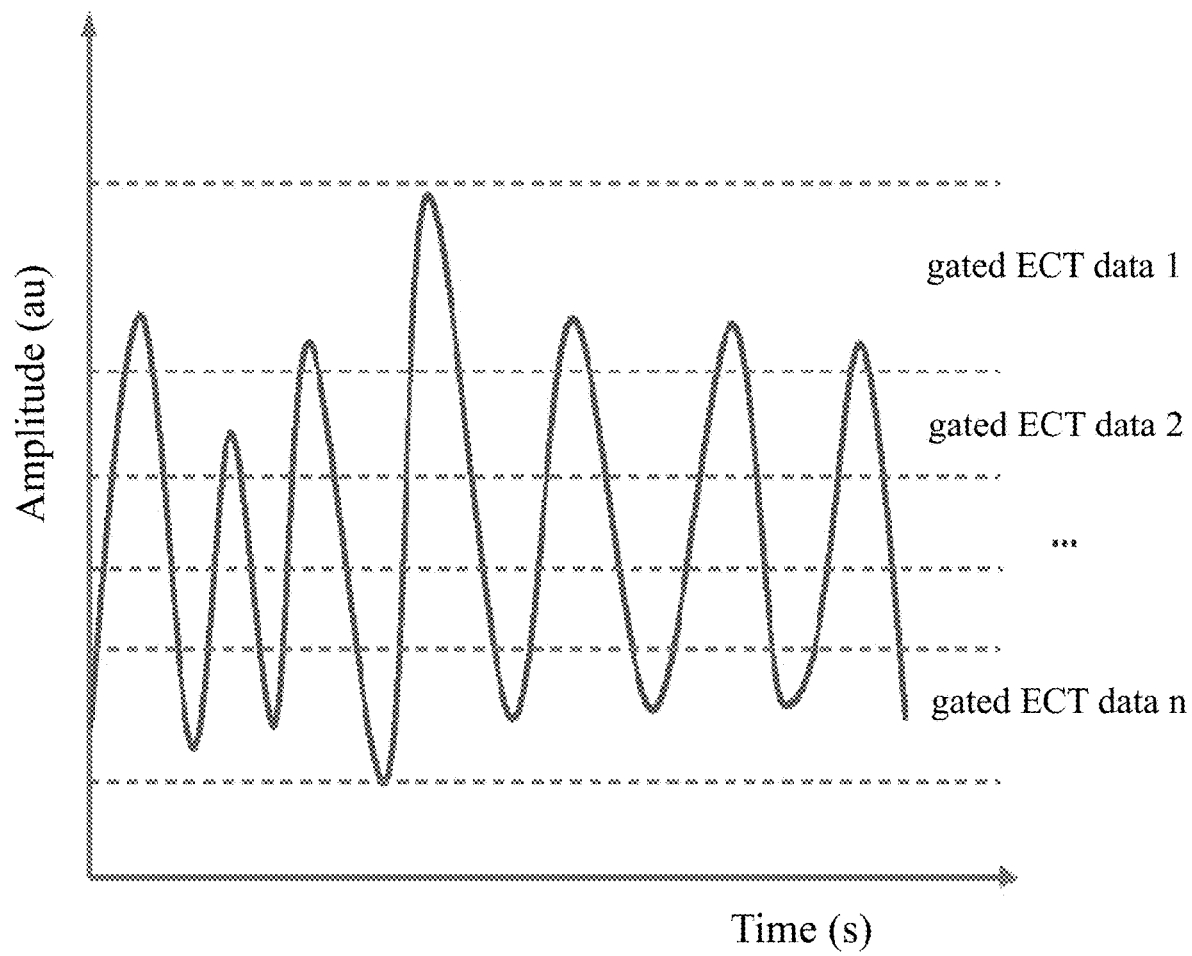
FIG. 12 illustrates a first exemplary division of a respiratory motion signal according to some embodiments of the present disclosure.

For example, as shown in FIG. 12, a respiratory motion signal may be divided into a first plurality of sections on the basis of the motion amplitude and also that each section of the respiratory motion signal corresponds to a same number of coincidence events. A section of the respiratory motion signal may include separate portions of the respiratory motion signal between two adjacent dashed lines. The amplitude interval of each of the first plurality of sections may be different.

Figure 13:
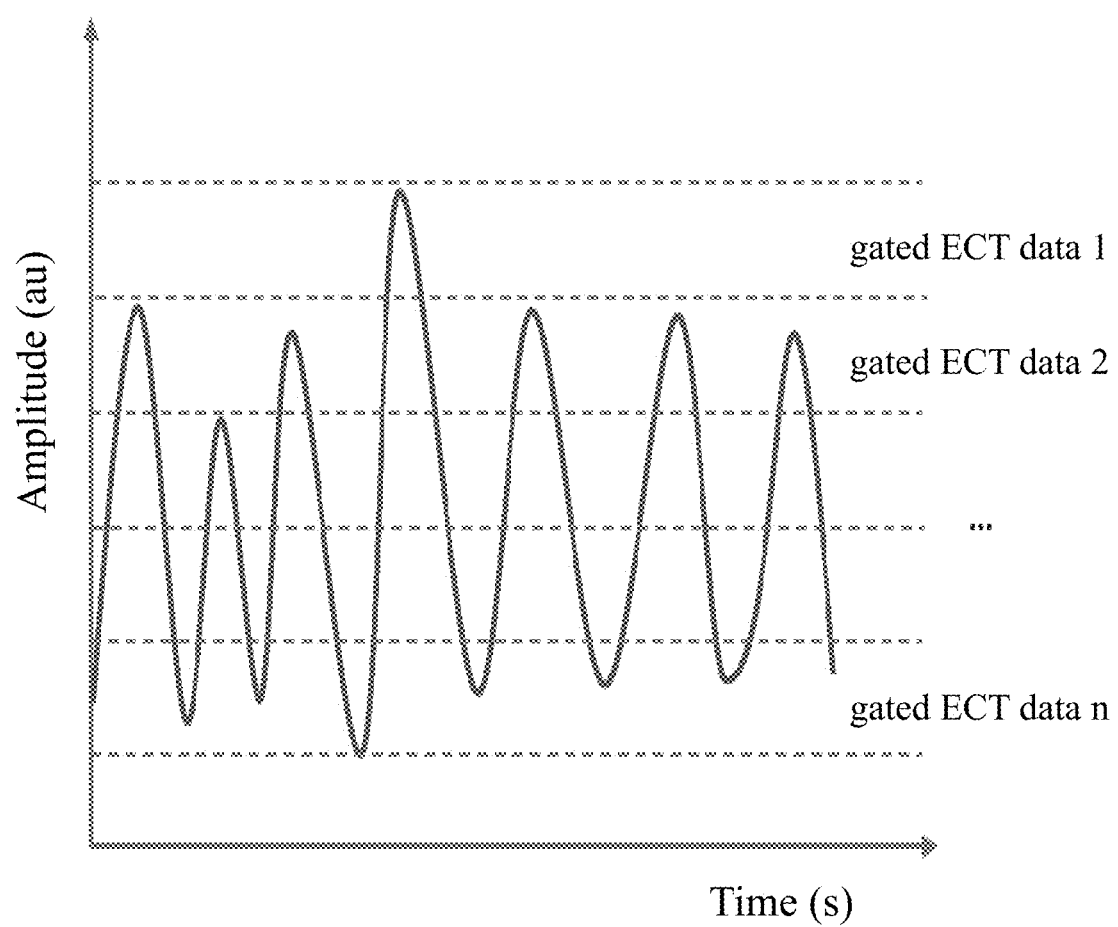
FIG. 13 illustrates a second exemplary division of a respiratory motion signal according to some embodiments of the present disclosure.

As another example, as shown in FIG. 13, a respiratory motion signal may be divided into a second plurality of sections on the basis that each section of the respiratory motion signal corresponds to a same amplitude interval. A section of the respiratory motion signal may include separate portions of the respiratory motion signal between two adjacent dashed lines. The number of coincidence events corresponding to each of the second plurality of sections may be different.

Figure 14:
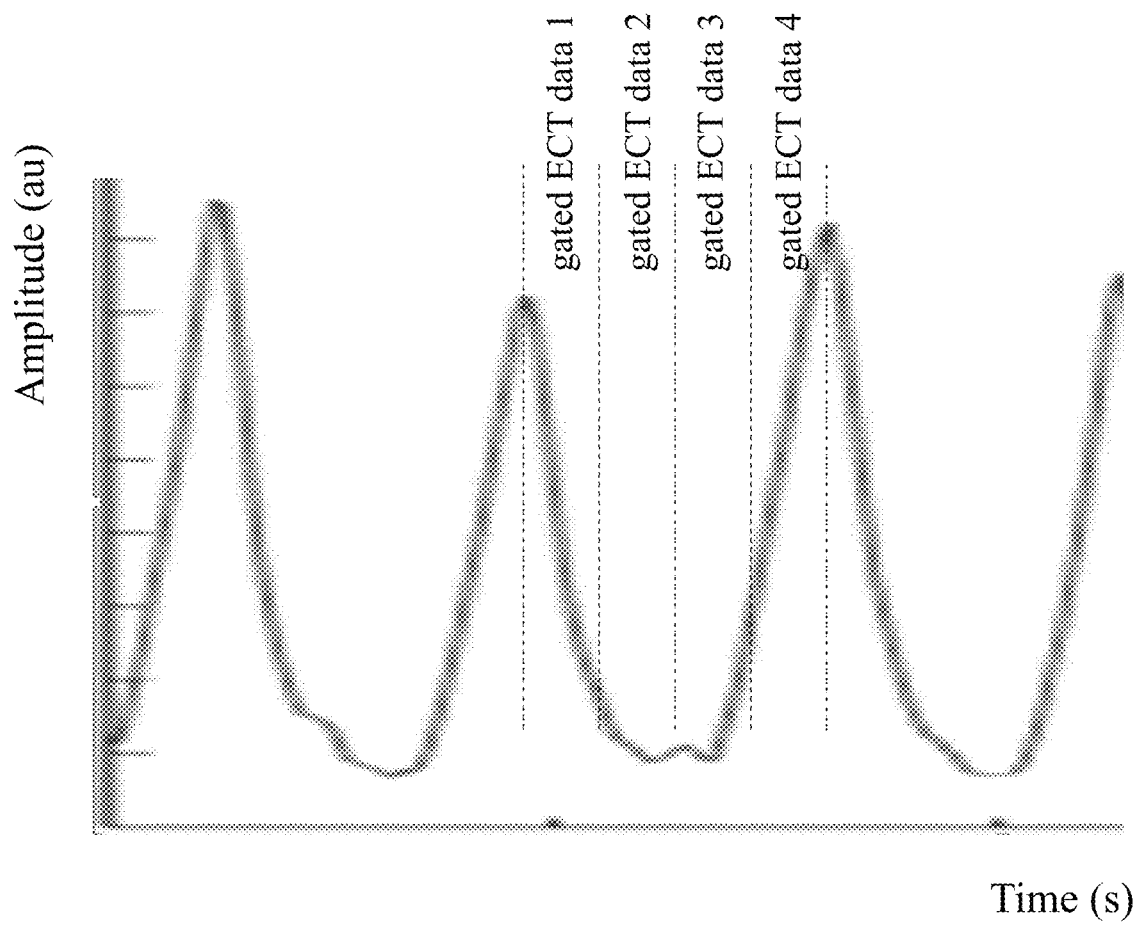
FIG. 14 illustrates a third exemplary division of a respiratory motion signal according to some embodiments of the present disclosure.

As a further example, as shown in FIG. 14, a respiratory motion signal may be divided into a third plurality of sections on the basis that each section of the respiratory motion signal corresponds to a same or different time intervals. In some embodiments, the third plurality of sections may be divided evenly during one respiratory cycle of the respiratory motion signal as shown in FIG. 14. In some embodiments, more than one respiratory cycle may be divided into a plurality of sub-sections, where each of the respiratory cycles may be divided similarly. A section of the third plurality of sections may include a sub-section in a same respiratory cycle or corresponding sub-sections in different respiratory cycles.

In 806, the ECT data may be gated based on the plurality of sections. In some embodiments, a section of the plurality of sections (e.g., the first plurality of sections, the second plurality of sections, or the third plurality of sections) of the motion signal may correspond to a range of time. The range of time may include a continuous time interval, or different discrete time intervals. The ECT data may be gated into a plurality of frames based on the plurality of sections such that a frame of ECT data may include coincidence events occurred in a same range of time.

Figure 9:
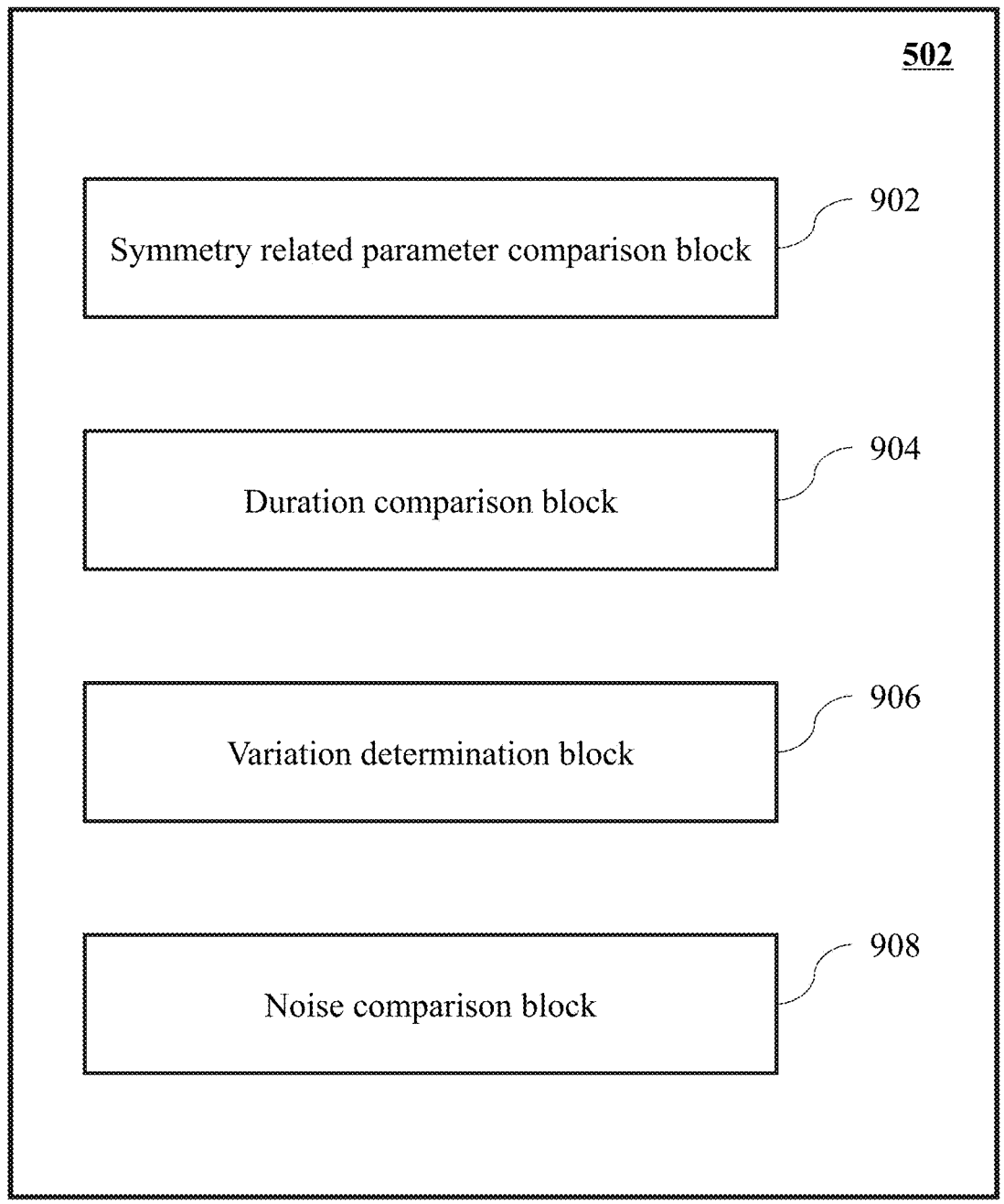
FIG. 9 is a block diagram illustrating an exemplary credibility determination sub-unit according to some embodiments of the present disclosure.

FIG. 9 is a block diagram illustrating exemplary credibility determination sub-unit 502 according to some embodiments of the present disclosure. The credibility determination sub-unit 502 may include a symmetry related parameter comparison block 902, a duration comparison block 904, a variation determination block 906, and a noise comparison block 908. The credibility determination sub-unit 502 may be implemented on various components (e.g., the processor 162 of the computing device 160 as illustrated in FIG. 1-C). For example, at least a portion of the credibility determination sub-unit 502 may be implemented on the computing device 160 as illustrated in FIG. 1-C or the mobile device 170 as illustrated in FIG. 1-D.

The credibility determination sub-unit 502 may determine the credibility of one or more values of a symmetry related parameter of a motion signal, as discussed elsewhere in the disclosure. In some embodiments, the credibility determination sub-unit 502 may obtain the motion signal, the one or more values of the symmetry related parameter from other modules and/or units of the processing engine 140, such as, the motion signal acquisition unit 202, and/or the symmetry related parameter determination unit 204. In some embodiments, the credibility determination sub-unit 502 may retrieve the motion signal, and/or the one or more values of the symmetry related parameter from may be retrieved from a storage device including, e.g., the storage 150, storage module 143, disk 167 and storage 179, an external storage device accessible by the system 100 or a portion thereof via, for example, the network 120, etc.

The symmetry related parameter comparison block 902 may compare one or more values of a symmetry related parameter with a first threshold. In some embodiments, the first threshold may relate to a value of the symmetry related parameter of the motion signal to assess symmetry or asymmetry of the motion signal with respect to a reference line. It should be noted for persons having ordinary skills in the art that the one or more values of the symmetry related parameter may relate to the asymmetry of the motion signal. The more asymmetrical the motion signal is, the greater the difference between the value(s) of the symmetry related parameter and the first threshold.

The duration comparison block 904 may compare a duration of the motion signal with a second threshold. In some embodiments, the duration of a respiratory motion signal may include a duration of the motion signal used to determine the value of the symmetry related parameter (e.g., $t_2-t_1$ in formula (5) or (6)). It should be noted for persons having ordinary skills in the art that the duration of the respiratory motion signal used to determine the value(s) of the symmetry related parameter should be long enough in order to reduce the effect of an incomplete respiratory cycle and/or insufficient information used in the determination of the value(s) of the symmetry related parameter. The second threshold may be selected based on the rhythm of the motion represented by the motion signal. For instance, for a cyclic motion (e.g., respiratory motion, cardiac motion, etc.), the second threshold may be at least 100%, or 120%, or 150%, or 180%, or 200%, etc., of the period (the duration of the time of one cycle) of the cyclic motion. In some embodiments, the period may be measured before or when the ECT data are acquired. In some embodiments, the period may be set based on empirical data by the system 100 or provided by a user (e.g., a doctor). For a same subject at different times, or for different subjects, the period or the suitable threshold may be the same or different, depending on various factors of the subject(s). Merely by way of example, the second threshold may be 100 seconds with respect to respiratory motion. The second threshold may be determined by a user through the console or the one or more terminals 130, or by the imaging system 100.

The variation determination block 906 may determine a variation of a set of values of a symmetry related parameter. The variation of the values may represent the consistency of the values of the symmetry related parameter. The variation of the set of values of the symmetry related parameter may be determined by comparing the set of values with a threshold or with each other. For example, as described elsewhere in the present disclosure, the threshold may be 0 in the situation that the set of values of the symmetry related parameter are determined based on formula (6) or (7). The variation determination block 906 may compare each of the set of values with 0. The one or more values of the symmetry related parameter may be determined as sufficiently consistent in the case that the set of values of the symmetry related parameter are positive or negative. Otherwise, the one or more values of the symmetry related parameter may be determined as inconsistent.

The noise comparison block 908 may determine a signal to noise ratio (SNR) of the motion signal and compare the SNR with a third threshold. The SNR may refer to the energy of signal over energy of noise in Fourier domain. Details regarding the determination of the SNR may be found in "Real-Time Data-Driven Respiratory Gating with Optimized Automatic VOI Selection," *Nuclear Science Symposium and Medical Imaging Conference (NSS/MIC)*, 2016 *IEEE*, 2016, the contents of which are incorporated herein by reference to its entirety. The third threshold may be determined by a user through the console or the one or more terminals 130, or by the imaging system 100.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, any blocks of the credibility determination sub-unit 502 may be removed or some blocks may be partially integrated in one or more independent blocks.

Figure 10:
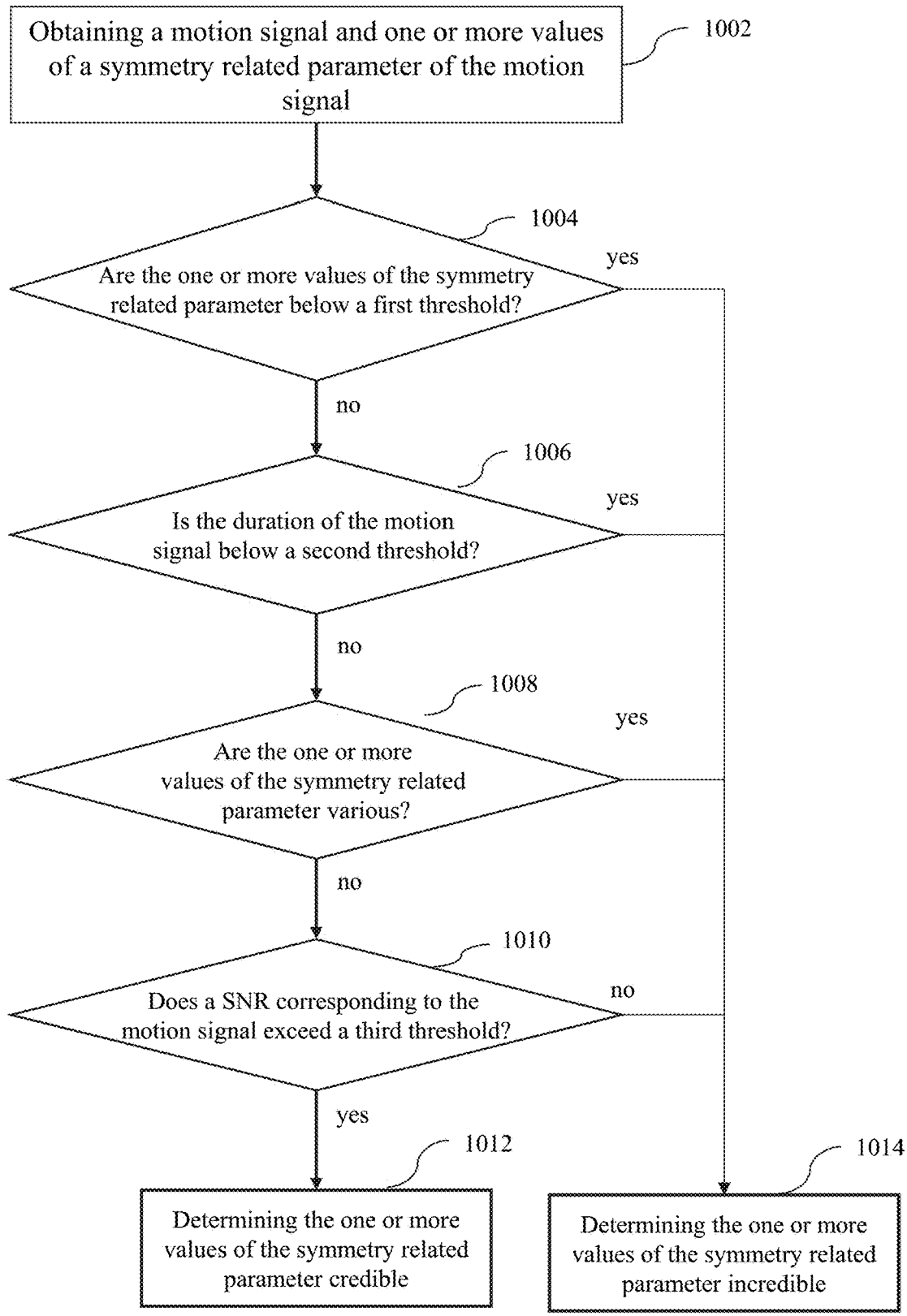
FIG. 10 is a flowchart illustrating an exemplary process for determining credibility of one or more values of a symmetry related parameter according to some embodiments of the present disclosure.

FIG. 10 is a flowchart illustrating an exemplary process for determining credibility of one or more values of a symmetry related parameter according to some embodiments of the present disclosure. The process 1000 may be performed by the credibility determination sub-unit 502. In some embodiments, the credibility of the one or more symmetry related parameters as illustrated in 604 in FIG. 6 may be determined according to the process 1000. The operations of the process 1000 presented herein are intended to be illustrative. In some embodiments, the process 1000 may be accomplished with one or more additional operations not described, and/or without one or more of the operations discussed. Additionally, the order in which the operations of the process as illustrated in FIG. 10 and described below in not intended to be limiting. In some embodiments, one or more operations of process 1000 illustrated in FIG. 10 for determining credibility of one or more values of a symmetry related parameter may be implemented in the imaging system 100 illustrated in FIG. 1-A. For example, the process 1000 illustrated in FIG. 10 may be stored in a storage (e.g., the storage 150) in the form of instructions, and invoked and/or executed by the processing engine 140 (e.g., the processor 162 of the computing device 160 as illustrated in FIG. 1-C, the GPU 173 or CPU 174 of the mobile device 170 as illustrated in FIG. 1-D).

In 1002, a motion signal and one or more values of a symmetry related parameter of the motion signal may be obtained. In some embodiments, the credibility determination sub-unit 502 may obtain a respiratory motion signal from the motion signal acquisition unit 202, and one or more values of the symmetry related parameter of the respiratory motion signal from the symmetry determination unit 204. In some embodiments, the credibility determination sub-unit 502 may retrieve the motion signal, and/or the one or more values of the symmetry related parameter from may be retrieved from a storage device including, e.g., the storage 150, storage module 143, disk 167 and storage 179, an external storage device accessible by the system 100 or a portion thereof via, for example, the network 120, etc.

In 1004, a determination may be made as to whether the one or more values of the symmetry related parameter are below a first threshold. In some embodiments, the determination may be made by the symmetry related parameter comparison block 902.

For illustration purposes, the symmetry related parameter comparison block 902 may compare the absolute value of each of the one or more values of the symmetry related parameter as illustrated in formula (6) with the first threshold. If the one or more values of the symmetry related parameter are below the first threshold, then the process 1000 may proceed to 1014; otherwise, the process 1000 may proceed to 1006. In some embodiments, the first threshold may be determined by a user through the one or more terminals 130. In some embodiments, the first threshold may be determined by the imaging system 100 based on, for example, empirical data, a default setting of the system 100, etc.

In 1006, a determination may be made as to whether a duration of the motion signal is less than a second threshold. In some embodiments, the determination may be performed by the duration comparison block 904. The selection of the second threshold may be performed based on the rhythm of the motion represented by the motion signal. See relevant description with reference to 904 in FIG. 9. For illustration purposes, the duration of the motion signal may include the duration of the respiratory motion signal (e.g., $t_2-t_1$ illustrated in formula (7)) used to determine the one or more values of the symmetry related parameter. The second threshold may include a value of time period determined by a user, e.g., 100 seconds. The duration comparison block 904 may compare the duration of the respiratory motion signal with the second threshold. If the duration of the respiratory motion signal is below the second threshold, the process 1000 may proceed to 1014; otherwise, the process 1000 may proceed to 1008.

In 1008, a determination may be made as to whether the one or more values of the symmetry related parameter are various or sufficiently consistent. In some embodiments, the determination may be performed by the variation determination block 906. For illustration purposes, if the one or more values of the symmetry related parameter as illustrated in formula (7) are all positive or negative, the variation determination block 906 may determine that the one or more values of the symmetry related parameter are sufficiently consistent; otherwise, the variation determination block 906 may determine that the one or more values of the symmetry related parameter are various or inconsistent. If the one or more values of the symmetry related parameter are determined to be inconsistent, the process 1000 may proceed to 1014; otherwise, the process 1000 may proceed to 1010.

In 1010, a determination may be made as to whether SNR corresponding to the motion signal exceeds a third threshold. In some embodiments, the determination may be performed by the noise determination block 908. If the SNR of the motion signal exceeds a third threshold, the process 1000 may proceed to 1012; otherwise, the process 1000 may proceed to 1014.

In 1012, the credibility of the one or more values of the symmetry related parameter may be determined as credible.

In 1014, the credibility of the one or more symmetry related parameters may be determined as incredible.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

For example, any operations of 1004, 1006, 1008, or 1010 may be omitted in the process 1000. For example, operation 1010 may be omitted, and the credibility determination sub-unit 502 may determine whether the one or more values of the symmetry related parameter are credible based on operations 1004, 1006, and 1008. As another example, all of 1004, 1006, 1008, 1010 may be omitted, and in such a case the credibility determination sub-unit 502 may consider the one or more values of the symmetry related parameter credible. In some embodiments, the order of the operations of the process 1000 may be changed or adjusted. For example, operation 1006 may be performed before 1004, or any two or more operations of 1004, 1006, 1008, and 1010 may be performed at the same time.

FIG. 11 illustrates an exemplary respiratory motion signal according to some embodiments of the present disclosure. As shown in FIG. 11, the amplitude of the respiratory motion signal changes over time. Different reference lines, such as, line α, line β, or line γ, are presented with respect to different exemplary techniques to determine a reference line as described in the disclosure. A candidate EIP and a candidate EEP are marked at a crest and a trough of the respiratory motion signal, respectively.

FIG. 12 illustrates a first exemplary division of a respiratory motion signal according to some embodiments of the present disclosure. As shown in FIG. 12, the respiratory motion signal is divided into n sections by the dashed lines. The ECT data may be gated into n frames based on the n sections. For example, the first section corresponds gated ECT data 1, . . . , and the last section corresponds to the gated ECT data n. The amplitude intervals of different sections may be different.

FIG. 13 illustrates a second exemplary division of a respiratory motion signal according to some embodiments of the present disclosure. As shown in FIG. 13, the respiratory motion signal is divided into n sections evenly in terms of the interval of the motion amplitude by the dashed lines.

FIG. 14 illustrates a third exemplary division of a respiratory motion signal according to some embodiments of the present disclosure. As shown in FIG. 14, a respiratory cycle of the respiratory motion signal is divided into four sections by the dashed lines. The time intervals of different sections may be the same or different.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on at least one machine each of which has at least one processor and storage, the method comprising:
acquiring a motion signal;
determining one or more values of a symmetry related parameter of the motion signal;
determining that the motion signal is flipped based on the one or more values of the symmetry related parameter; and
correcting, in response to the determination that the motion signal is flipped, the motion signal,
wherein the motion signal comprises a respiratory motion signal, and the determining one or more values of a symmetry related parameter of the motion signal comprises:
identifying an end of a candidate inspiration phase (candidate EIP) and an end of a candidate expiration phase (candidate EEP) in the respiratory motion signal, wherein an amplitude of the candidate EIP is a peak amplitude of the respiratory motion signal, and an amplitude of the candidate EEP is a valley amplitude of the respiratory motion signal; and
determining, based on the candidate EIP and the candidate EEP, a reference line with respect to the motion signal.

2. The method of claim 1, the acquiring a motion signal comprising:
acquiring a respiratory motion signal based on Emission Computed Tomography (ECT) data.

3. The method of claim 1, wherein the reference line is midway between the candidate EIP and the candidate EEP such that the amplitude of the candidate EIP is equal to the amplitude of the candidate EEP;
and the determining one or more values of a symmetry related parameter of the motion signal comprises:
determining the one or more values of the symmetry related parameter of the motion signal based on a duration related to the candidate EIP and a duration related to the candidate EEP.

4. The method of claim 1, the determining one or more values of a symmetry related parameter of the motion signal comprising:
determining a duration related to the candidate inspiration phase and a duration of the candidate expiration phase based on the reference line, wherein the reference line is such that the duration of the candidate inspiration phase is equal to the duration of the candidate expiration phase;
identifying one or more candidate EIPs and one or more candidate EEPs;
determining a peak amplitude of the one or more candidate EIPs of the motion signal with respect to the reference line, and a valley amplitude of the one or more candidate EEPs of the motion signal with respect to the reference line; and
determining the one or more values of the symmetry related parameter of the motion signal based on the peak amplitude and the valley amplitude.

5. The method of claim 1, the determining a reference line of the motion signal comprising:
determining the reference line of the respiratory motion signal based on a first criterion including a combination of an amplitude and a duration of the respiratory motion signal.

6. The method of claim 5, the determining one or more values of a symmetry related parameter of the motion signal comprising:
determining one or more values of the symmetry related parameter of the respiratory motion signal based on a second criterion including a combination of a weighted amplitude and the duration of the respiratory motion signal with respect to the reference line.

7. The method of claim 1, the determining that the motion signal is flipped comprising:

determining credibility of the one or more values of the symmetry related parameter.

8. The method of claim 7, the determining credibility of the one or more values of the symmetry related parameter comprising:
determining whether the one or more values of the symmetry related parameter are below a first threshold; or
determining whether a duration of the respiratory motion signal is less than a second threshold; or
determining a variation among the one or more values of the symmetry related parameter; or
determining whether a signal to noise ratio corresponding to the respiratory motion signal exceeds a third threshold.

9. The method of claim 7, the determining that the motion signal is flipped comprising:
determining, in response to a determination that the one or more values of the symmetry related parameter are incredible, that the respiratory motion signal is flipped based on a plurality of images reconstructed based on the ECT data.

10. The method of claim 9, the determining that the respiratory motion signal is flipped based on a plurality of images reconstructed based on the ECT data further comprising:
gating, based on the respiratory motion signal, the ECT data into a plurality of frames;
reconstructing the plurality of images, an image of the plurality of images corresponding to a frame of the plurality of frames of the ECT data;
registering at least two of the plurality of images;
determining a motion of a point of interest based on the registration; and
determining that the respiratory motion signal is flipped based on the motion of the point of interest.

11. The method of claim 10, wherein each frame of the plurality of frames of the ECT data corresponds to a same number of ECT events.

12. The method of claim 10, wherein each frame of the plurality of frames of the ECT data corresponds to a same amplitude interval, or a same time interval.

13. The method of claim 10, the registering at least two of the plurality of images comprising:
registering the at least two of the plurality of images based on an approach of sum square error (SSE).

14. A system, comprising:
at least one non-transitory computer-readable storage medium including a set of instructions;
at least one processor in communication with the at least one computer-readable storage medium, wherein when executing the set of instructions, the at least one processor is directed to:
acquire a respiratory motion signal based on ECT data;
determine one or more values of a symmetry related parameter of the respiratory motion signal;
determine, based on the one or more values of the symmetry related parameter, that the respiratory motion signal is flipped; and
correct, in response to the determination that the respiratory motion signal is flipped, the respiratory motion signal,
wherein the motion signal comprises a respiratory motion signal, and the at least one processor is further directed to:
identify an end of a candidate inspiration phase (candidate EIP) and an end of a candidate expiration phase (candidate EEP) in the respiratory motion signal based on the reference line, wherein an amplitude of the candidate EIP is a peak amplitude of the respiratory motion signal, and an amplitude of the candidate EEP is a valley amplitude of the respiratory motion signal; and
determining, based on the candidate EIP and the candidate EEP, a reference line with respect to the motion signal.

15. The system of claim 14, wherein the at least one processor is further directed to:
determine a reference line with respect to the respiratory motion signal, wherein the one or more values of the symmetry related parameter of the respiratory motion signal are determined based on the reference line.

16. The system of claim 14, wherein the at least one processor is further directed to:
determine that the one or more values of the symmetry related parameter are incredible;
in response to the determination that the one or more values of the symmetry related parameter are incredible,
gate, based on the respiratory motion signal, the ECT data into a plurality of frames;
reconstruct a plurality of images, an image of the plurality of images corresponding to a frame of the plurality of frames of the ECT data;
register at least two of the plurality of images;
determine a motion of a point of interest based on the registration; and
determine, based on the motion of the point of interest, that the respiratory motion signal is flipped.

17. A method implemented on at least one machine each of which has at least one processor and storage, the method comprising:
acquiring Emission Computed Tomography (ECT) data of a subject;
determining a motion signal based on the ECT data;
determining one or more values of a symmetry related parameter of the motion signal;
determining that the motion signal is flipped based on the one or more values of the symmetry related parameter; and
correcting, in response to the determination that the motion signal is flipped, the motion signal,
wherein the motion signal comprises a respiratory motion signal, and the determining one or more values of a symmetry related parameter of the motion signal comprises:
identifying an end of a candidate inspiration phase (candidate EIP) and an end of a candidate expiration phase (candidate EEP) in the respiratory motion signal based on the reference line, wherein an amplitude of the candidate EIP is a peak amplitude of the respiratory motion signal, and an amplitude of the candidate EEP is a valley amplitude of the respiratory motion signal; and
determining, based on the candidate EIP and the candidate EEP, a reference line with respect to the motion signal.

18. The method of claim 17, further comprising:
reconstructing a plurality of images, each of the plurality of images corresponding to a frame of the ECT data;
determining a motion of a point of interest based on a registration between at least two of the plurality of images; and
determining that the motion signal is flipped based on the one or more values of the symmetry related parameter and the motion of the point of interest.

* * * * *